United States Patent
Garcia et al.

(10) Patent No.: US 11,646,102 B2
(45) Date of Patent: May 9, 2023

(54) SYSTEM AND METHOD FOR SECONDARY ANALYSIS OF NUCLEOTIDE SEQUENCING DATA

(71) Applicant: ILLUMINA, INC., San Diego, CA (US)

(72) Inventors: Francisco Jose Garcia, Rancho Santa Fe, CA (US); Come Raczy, Del Mar, CA (US); Aaron Day, San Diego, CA (US); Michael J. Carney, San Diego, CA (US)

(73) Assignee: ILLUMINA, INC.

( * ) Notice: Subject to any disclaimer, the term of this patent is extended or adjusted under 35 U.S.C. 154(b) by 982 days.

(21) Appl. No.: 16/311,141

(22) PCT Filed: Oct. 6, 2017

(86) PCT No.: PCT/US2017/055653
§ 371 (c)(1),
(2) Date: Dec. 18, 2018

(87) PCT Pub. No.: WO2018/068014
PCT Pub. Date: Apr. 12, 2018

(65) Prior Publication Data
US 2019/0385699 A1 Dec. 19, 2019

Related U.S. Application Data

(60) Provisional application No. 62/405,824, filed on Oct. 7, 2016.

(51) Int. Cl.
*G16B 30/10* (2019.01)
*G16B 20/20* (2019.01)
*C12Q 1/68* (2018.01)

(52) U.S. Cl.
CPC ............... *G16B 30/10* (2019.02); *C12Q 1/68* (2013.01); *G16B 20/20* (2019.02)

(58) Field of Classification Search
CPC ........... G16B 30/10; G16B 20/20; C12Q 1/68
(Continued)

(56) References Cited

U.S. PATENT DOCUMENTS

2003/0120429 A1   6/2003   Li et al.
2011/0270533 A1   11/2011  Zhang et al.
(Continued)

FOREIGN PATENT DOCUMENTS

EP    2808814 A2    12/2014
RU    2539038 C1    1/2015

OTHER PUBLICATIONS

Gavin R Oliver, Steven N Hart, Eric W Klee: Bioinformatics for Clinical Next Generation Sequencing, Clinical Chemistry 61:1, 124-135 (2015). (Year: 2015).*
(Continued)

*Primary Examiner* — G Steven Vanni
*Assistant Examiner* — Guozhen Liu
(74) *Attorney, Agent, or Firm* — Knobbe, Martens, Olson & Bear LLP

(57) ABSTRACT

Disclosed herein are systems and methods for performing secondary analyses of nucleotide sequencing data in a time-efficient manner. Some embodiments include performing a secondary analysis iteratively while sequence reads are generated by a sequencing system. Secondary analyses can encompass both alignment of sequence reads to a reference sequence (e.g., the human reference genome sequence) and utilization of this alignment to detect differences between a sample and the reference. Secondary analysis can enable detection of genetic differences, variant detection and genotyping, identification of single nucleotide polymorphisms
(Continued)

(SNPs), small insertions and deletion (indels) and structural changes in the DNA, such as copy number variants (CNVs) and chromosomal rearrangements.

36 Claims, 15 Drawing Sheets

(58) Field of Classification Search
USPC .......................................................... 702/20
See application file for complete search history.

(56) References Cited

U.S. PATENT DOCUMENTS

| | | | |
|---|---|---|---|
| 2012/0203792 | A1 | 8/2012 | Zheng et al. |
| 2013/0338933 | A1* | 12/2013 | Deciu .................... G16B 30/00 702/20 |
| 2014/0121987 | A1 | 5/2014 | Park |
| 2014/0180594 | A1* | 6/2014 | Kim ....................... G16B 30/10 702/19 |
| 2014/0238250 | A1 | 8/2014 | Gephart et al. |
| 2014/0242588 | A1* | 8/2014 | Van Den Boom ..... G16B 20/00 702/20 |
| 2016/0034638 | A1* | 2/2016 | Spence .................. G16B 30/10 702/19 |

OTHER PUBLICATIONS

M Dodt, JT Roehr, R Ahmed, C Dieterich, FLEXBAR—flexible barcode and adapter processing for next-generation sequencing platforms, Biology 2012, 1(3), 895-905 (Year: 2012).*

Karl V. Voelkerding, Shale A. Dames, and Jacob D. Durtschi: Next-Generation Sequencing: From Basic Research to Diagnostics. Clinical Chemistry 55:4 641-658 (2009) (Year: 2009).*

Homer, N., Nelson, S.F. Improved variant discovery through local re-alignment of short-read next-generation sequencing data using SRMA. Genome Biol 11, R99 (2010). https://doi.org/10.1186/gb-2010-11-10-r99 (Year: 2010).*

Loose, M., Malla, S. & Stout, M. Real-time selective sequencing using nanopore technology. Nat Methods 13, 751-754 (2016). https://doi.org/10.1038/nmeth.3930. Published Jul. 25, 2016 (Year: 2016).*

Moorthie, S., et al., "Informatics and clinical genome sequencing: opening the black box", Genertics in Medicine 15 (3) doi: 10.1038/gim.2012.116, Sep. 13, 2012, 165-171.

Muzzey, D., et al., "Understanding the Basics of NGS: From Mechanism to Variant Calling", Curr. Genet. Med. Rep. (4): 158-165. doi: 10.1007/s40142-015-0076-8., Sep. 4, 2015, 158-165.

Oliver, G., et al., "Bioinformatics for clinical next generation sequencing", Clin. Chem 61(1) doi: 10.1373/clinchem.2014. 224360, Jan. 2015, 124-135.

Robasky, K., et al., "The role of replicates for error mitigation in next-generation sequencing", Nat. Rev. Genet. 15(1):56-62. doi: 10.1038/nrg3655., Jan. 2014, 56-62.

AU Application 2017341069, Examination Report No. 3, dated Jul. 22, 2020, pp. 1-6.

Notice of Allowance issued in application No. RU 2018143972/10(073329), dated Nov. 25, 2020.

Zhong, C., et al., "GRASP: Guided Reference-based Assembly of Short Peptides", Nucleic Acids Research 43(3)e18 doi: 10.1093/nar/gku1210, Nov. 20, 2014, 1-10.

Illumina. "Illumina/Strelka." GitHub, Feb. 6, 2019, github.com/Illumina/strelka.

Lindner, Martin S., et al. "HiLive: real-time mapping of illumina reads while sequencing." Bioinformatics 33.6 (2017): 917-319.

Saunders et al. "Strelka: accurate somatic small-variant calling from sequenced tumor-normal sample pairs." *Genome analysis*, vol. 28, No. 14, May 10, 2012, Bioinformatics, pp. 1811-1817.

Miller et al., "Assembly algorithms for next-generation sequencing data," *Genomics*, vol. 95, No. 6, Jun. 1, 2010, Academic Press, San Diego, pp. 315-327.

International Search Report and Written Opinion dated Jan. 29, 2018 in related International Application No. PCT/US2017/055653.

Zhong et al., Metagenome and Metatranscript Analyses Using Protein Family Profiles, PLOS Computational Biology, Jul. 11, 2016, pp. 1-22.

Zhong et al., GRASPx: Efficient Homolog-search of Short Peptide Metagenome Database Through Simultaneous alignment and Assembly, BMC Bioinformatics, vol. 17, No. 8, Aug. 31, 2018, pp. 611-621.

* cited by examiner

US 11,646,102 B2

SYSTEM AND METHOD FOR SECONDARY ANALYSIS OF NUCLEOTIDE SEQUENCING DATA

RELATED APPLICATIONS

The present application is a U.S. national phase application under 35 U.S.C. § 371 of International Application No. PCT/US/2017/055653, filed Oct. 6, 2017 and published in English as WO 2018/068014 A1 on Apr. 12, 2018, which claims priority to U.S. Provisional Application No. 62/405,824, filed Oct. 7, 2016. The content of each of these related applications is incorporated herein by reference in its entirety.

BACKGROUND

Field

The present disclosure relates generally to the field of DNA sequencing, and more particularly relates to systems and methods for performing real-time secondary analyses for next generation sequencing application.

Description of the Related Art

Genetic mutation can be identified by identifying variants—relative to reference sequences—in sequence reads. To identify a variant, a sample from a subject may be completely sequenced using a sequencing instrument to obtain sequence reads. After obtaining sequence reads, the sequence reads can be assembled or aligned prior to variant calling. Thus, identifying variants includes distinct steps that are performed sequentially and can be time consuming to perform after the conclusion of the sequencing process.

SUMMARY

Disclosed herein are systems and methods for sequencing polynucleotides. In one embodiment, the system comprises: a memory comprising a reference nucleotide sequence; a processor configured to execute instructions that perform a method comprising: receiving a first nucleotide subsequence of a read from a sequencing system; processing the first nucleotide subsequence using a first alignment path to determine a first plurality of candidate locations of the read on the reference sequence; determining whether the first nucleotide subsequence aligns to the reference sequence based on the determined candidate locations; receiving a second nucleotide subsequence from the sequencing system; processing the second nucleotide subsequence to determine a second plurality of candidate locations of the read that align to the reference sequence using: a second alignment path if the read is aligned to the reference sequence, and the first alignment path if otherwise, wherein the second alignment path is more computationally efficient than the first alignment path to determine the second plurality of candidate locations of the read.

In one embodiment, the method comprises: receiving a first nucleotide subsequence from a sequencing system during a sequencing run; and performing a secondary analysis of the first nucleotide subsequence of a read based on a reference sequence using a first analysis path or a second analysis path, wherein the second analysis path is more computationally efficient than the first processing path in performing the secondary analysis.

DETAILED DESCRIPTION

Figure 1:
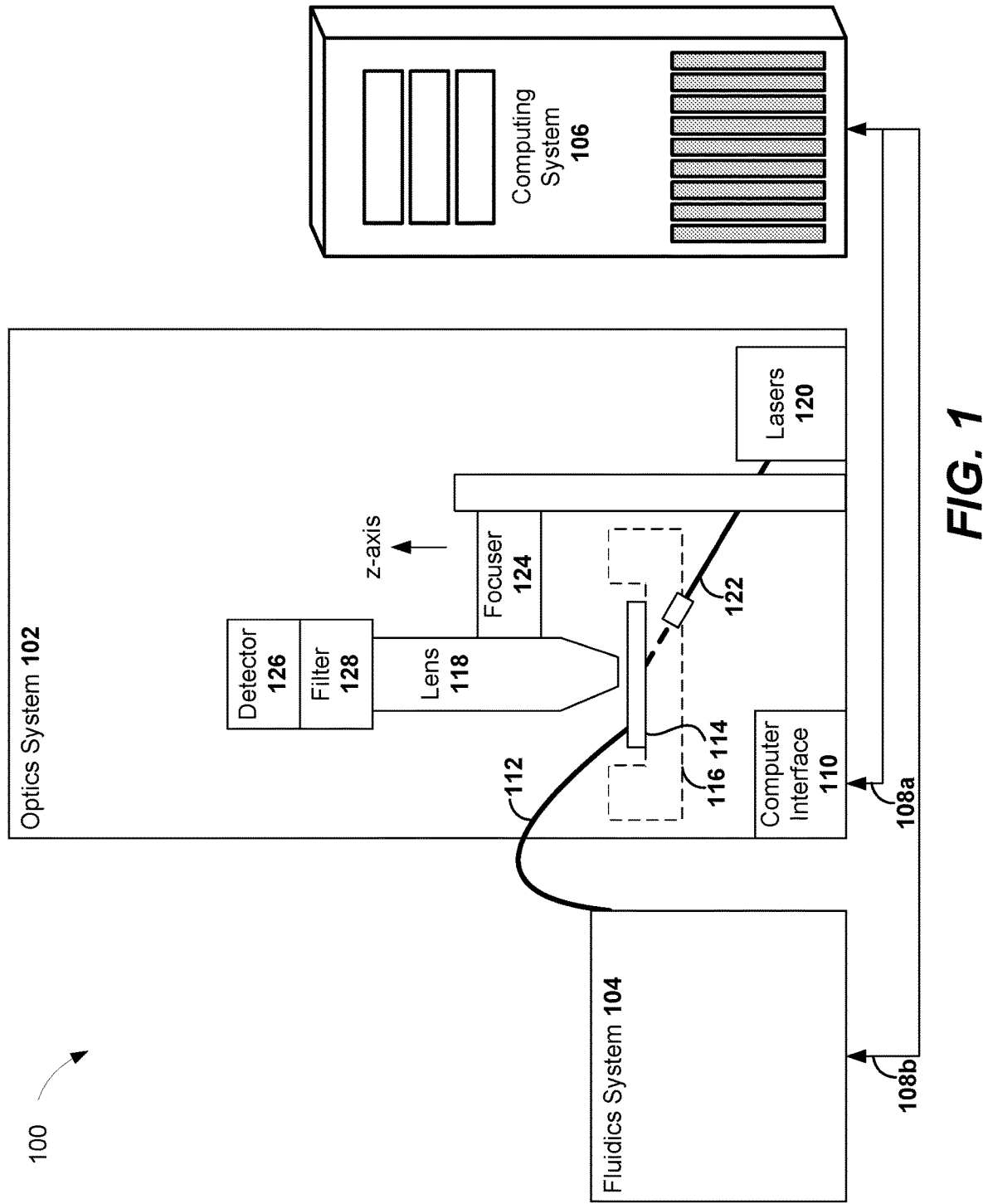
FIG. 1 is a schematic illustration showing an example sequencing system for performing real-time analyses.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Disclosed herein are systems and methods for performing secondary analyses of nucleotide sequencing data in a time-efficient manner. In some embodiments, the method comprises performing a secondary analysis iteratively while sequence reads are generated by a sequencing system. Secondary analyses can encompass both alignment of sequence reads to a reference sequence (e.g., the human reference genome sequence) and utilization of this alignment to detect differences between a sample and the reference. Secondary analyses can enable detection of genetic differences, variant detection and genotyping, identification of single nucleotide polymorphisms (SNPs), small insertions and deletion (indels) and structural changes in the DNA, such as copy number variants (CNVs) and chromosomal rearrangements.

By performing secondary analyses while sequence, reads are generated, the system and method can determine preliminary variant calls iteratively in real-time (or with zero or low latency). Final results of variant determinations may be available soon after (or immediately after) the end of a sequencing run. Alternatively, a sequencing run can be terminated early if variant calls are available with sufficient confidence during the run. In some embodiments, only information related to variant determinations (e.g., variant calls) is transferred off the sequencing system. This can decrease, or minimize, the data bandwidth required in comparison to performing the variant determinations in a system that is external. In addition, only variant information may be sent to a computing system (e.g., a cloud computing system) for further processing. In this embodiment, sequencing runs may be terminated prior to completion of an entire sequencing process. For example, if the identity of a pathogen of interest is determined after a number of sequencing cycles of a sequencing run, the sequencing run can be terminated. Thus, the time to a particular answer (e.g., pathogen identification) may be decreased. In one embodiment, outputs and intermediate results of the system can include histograms of duplicates, exact matches, single and double SNPs, and single and double indels.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N Y 1989). For purposes of the present disclosure, the following terms are defined below.
Sequencer for Performing Real-Time Secondary Analyses Disclosed herein are systems and methods for performing secondary analyses iteratively in a time and/or computing resource efficient manner. Secondary analyses can encompass both alignment of sequence reads to a reference sequence (e.g., the human reference genome sequence) and utilization of this alignment to detect differences between a sample and the reference. Secondary analyses can enable detection of genetic differences, variant detection and genotyping, identification of single nucleotide polymorphisms (SNPs), small insertions and deletion (indels) and structural changes in the DNA, such as copy number variants (CNVs) and chromosomal rearrangements. Secondary analyses may be performed for one sequencing cycle while sequencing data is being generated for the next sequencing cycle.

FIG. 1 is a schematic illustration showing an example sequencing system 100 for performing real-time secondary analyses. Non-limiting examples of the sequencing method utilized by the sequencing system 100 can include sequencing by synthesis and Heliscope single molecule sequencing. The sequencing system 100 can include an optics system 102 configured to generate raw sequencing data using sequencing reagents supplied by a fluidics system 104 that is part of the sequencing system 100. The raw sequencing data can include fluorescent images captured by the optics system 102. A computer system 106 that is part of the sequencing system 100 can be configured to control the optics system 102 and the fluidics system 104 via communication channels 108a and 108b. For example, a computer interface 110 of the optics system 102 can be configured to communicate with the computer system 106 through the communication channel 108a.

During sequencing reactions, the fluidics system 104 can direct the flow of reagents through one or more reagent tubes 112 to and from a flowcell 114 positioned on a mounting stage 116. The reagents can be, for example, fluorescently labeled nucleotides, buffers, enzymes, and cleavage reagents. The flowcell 114 can include at least one fluidic channel. The flowcell 114 can be a patterned array flowcell or a random array flowcell. The flowcell 114 can include multiple clusters of single-stranded polynucleotides to be sequenced in the at least one fluidic channel. The lengths of the polynucleotides can vary ranging, for example, from 200 bases to 1000 bases. The polynucleotides can be attached to the one or more fluidic channels of the flowcell 114. In some embodiments, the flowcell 114 can include a plurality of beads, wherein each bead can include multiple copies of a polynucleotide to be sequenced. The mounting stage 116 can be configured to allow proper alignment and movement of the flowcell 114 in relation to the other components of the optics system 102. In one embodiment, the mounting stage 116 can be used to align the flowcell 114 with a lens 118.

The optics system 102 can include multiple lasers 120 configured to generate light at predetermined wavelengths. The light generated by the lasers 120 can pass through a fiber optic cable 122 to excite fluorescent labels in the flowcell 114. The lens 118, mounted on a focuser 124, can move along the z-axis. The focused fluorescent emissions can be detected by a detector 126, for example a charge-coupled device (CCD) sensor or a complementary metal oxide semiconductor (CMOS) sensor.

A filter assembly 128 of the optics system 102 can be configured to filter the fluorescent emissions of the fluorescent labels in the flowcell 114. The filter assembly 128 can include a first filter and a second filter. Each filter can be a longpass filter, a shortpass filter, or a bandpass filter, depending on the types of fluorescent molecules being used in the system. The first filter can be configured to detect the fluorescent emissions of the first fluorescent labels by the detector 126. The second filter can be configured to detect the fluorescent emissions of the second fluorescent labels by the detector 126. With two filters in the filter assembly 128, the detector 126 can detect two different wavelengths of fluorescent emissions.

In some embodiments, the optics system 102 can include a dichroic configured to split the fluorescent emissions. The optics system 102 can include two detectors, a first detector coupled with a first filter for detecting fluorescent emissions at a first wavelength and a second detector coupled with a second filter for detecting fluorescent emissions at a second wavelength.

Figure 2:
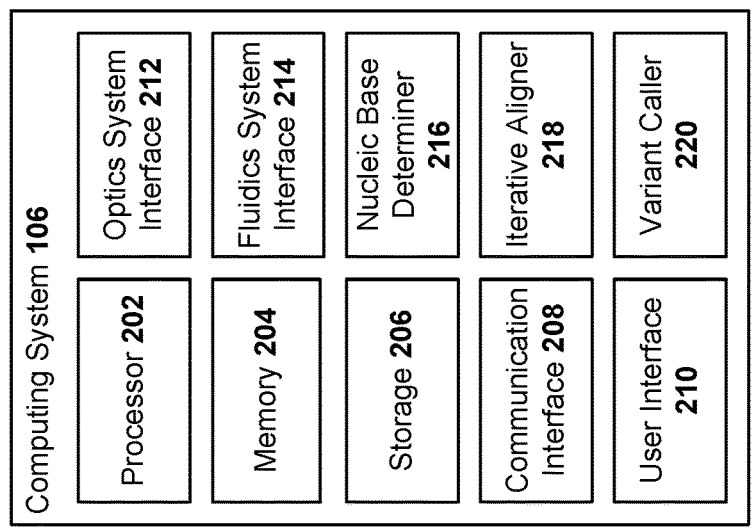
FIG. 2 shows a functional block diagram of an example computer system for performing real-time analyses.

In use, a sample having a polynucleotide to be sequenced is loaded into the flowcell 114 and placed in the mounting stage 116. The computer system 106 then activates the fluidics system 104 to begin a sequencing cycle. During sequencing reactions, the computer system 106 instructs the fluidics system 104, through the communication interface 108b, to supply reagents, for example nucleotide analogs, to the flowcell 114. Through the communication interface 108a and the computer interface 110, the computer system 106 is configured to control the lasers 120 of the optics system 102 to generate light at a predetermined wavelength and shine onto nucleotide analogs coupled with fluorescent labels incorporated into growing primers hybridized to polynucleotides being sequenced. The computer system 106 controls the detector 126 of the optics system 102 to capture the emission spectra of the nucleotide analogs in fluorescent images. The computer system 106 receives the fluorescent images from the detector 126 and process the fluorescent images received to determine the nucleotide sequence of the polynucleotides being sequenced.
Computer System The computer system 106 of the sequencing system 100 can be configured to control the optics system 102 and the fluidics system 104 as discussed above. While many configurations are possible for the computer system 106, one embodiment is illustrated in FIG. 2. As shown in FIG. 2, the computer system 106 can include a processor 202 that is in electrical communication with a memory 204, a storage 206, and a communication interface 208. In one embodiment, the computer system 106 includes a field-programmable gate array (FPGA), graphics processing unit (GPU), and/or vector central processing unit (CPU) to perform sequence alignments and generate variant calls.

The processor 202 can be configured to execute instructions that cause the fluidics system 104 to supply reagents to the flowcell 114 during sequencing reactions. The processor 202 can execute instructions that control the lasers 120 of the optics system 102 to generate light at predetermined wavelengths. The processor 202 can execute instructions that control the detector 126 of the optics system 102 and receive data from the detector 126. The processor 202 can execute instructions to process data, for example fluorescent images, received from the detector 126 and to determine the nucleotide sequence of polynucleotides based on the data received form the detector 126.

The memory 204 can be configured to store instructions for configuring the processor 202 to perform the functions of the computer system 106 when the sequencing system 100 is powered on. When the sequencing system 100 is powered off, the storage 206 can store the instructions for configuring the processor 202 to perform the functions of the computer system 106. The communication interface 208 can be configured to facilitate the communications between the computer system 106, the optics system 102, and the fluidics system 104.

The computer system 106 can include a user interface 210 configured to communicate with a display device (not shown) for displaying the sequencing results (including results of secondary analyses such as variant callings) of the sequencing system 100. The user interface 210 can be configured to receive inputs from users of the sequencing system 100. An optics system interface 212 and a fluidics system interface 214 of the computer system 106 can be configured to control the optics system 102 and the fluidics system 104 through the communication links 108a and 108b illustrated in FIG. 1. For example, the optics system interface 212 can communicate with the computer interface 110 of the optics system 102 through the communication link 108a.

The computer system 106 can include a nucleic base determiner 216 configured to determine the nucleotide sequence of polynucleotides using the data received from the detector 126. The nucleic base determiner 216 can generate a template of the locations of polynucleotide clusters in the flowcell 114 using the fluorescent images captured by the detector 126. The nucleic base determiner 216 can register the locations of polynucleotide clusters in the flowcell 114 in the fluorescent images captured by the detector 126 based on the location template generated. The nucleic base determiner 216 can extract intensities of the fluorescent emissions from the fluorescent images to generate extracted intensities. The nucleic base determiner 216 can determine the bases of the polynucleotide from the extracted intensities. The nucleic base determiner 216 can determine quality scores of the bases of the polynucleotides determined.

The computer system 106 can include an iterative aligner 218 and a variant caller 220, such as the Strelka variant caller (sites.google.com/site/strelkasomaticvariantcaller/home/faq). During a sequencing cycle, the iterative aligner 218 can align sequence reads determined by the nucleic base determiner 216 to a reference sequence. The aligned sequence reads can have associated scores. The scores can be probabilities (e.g., mismatch percentages) that the sequence reads have been correctly aligned to the reference sequence. In some implementations, the computer system 106 can include hardware, such as a field-programmable gate array (FPGA) or a graphics processing unit (GPU), for aligning sequence reads to the reference sequence and for determining variant calls. In some embodiments, the iterative aligner 218 and the variant caller 220 can be implemented by a computer system distinct from the computer system 106. In some embodiments, the computer system 106 may be an integrated component of the sequencing system 100. In some embodiments, the optics system 102, the fluidics system 104, and/or the computer system 106 can be integrated into one machine.

Sequencing by Synthesis

Figure 3:
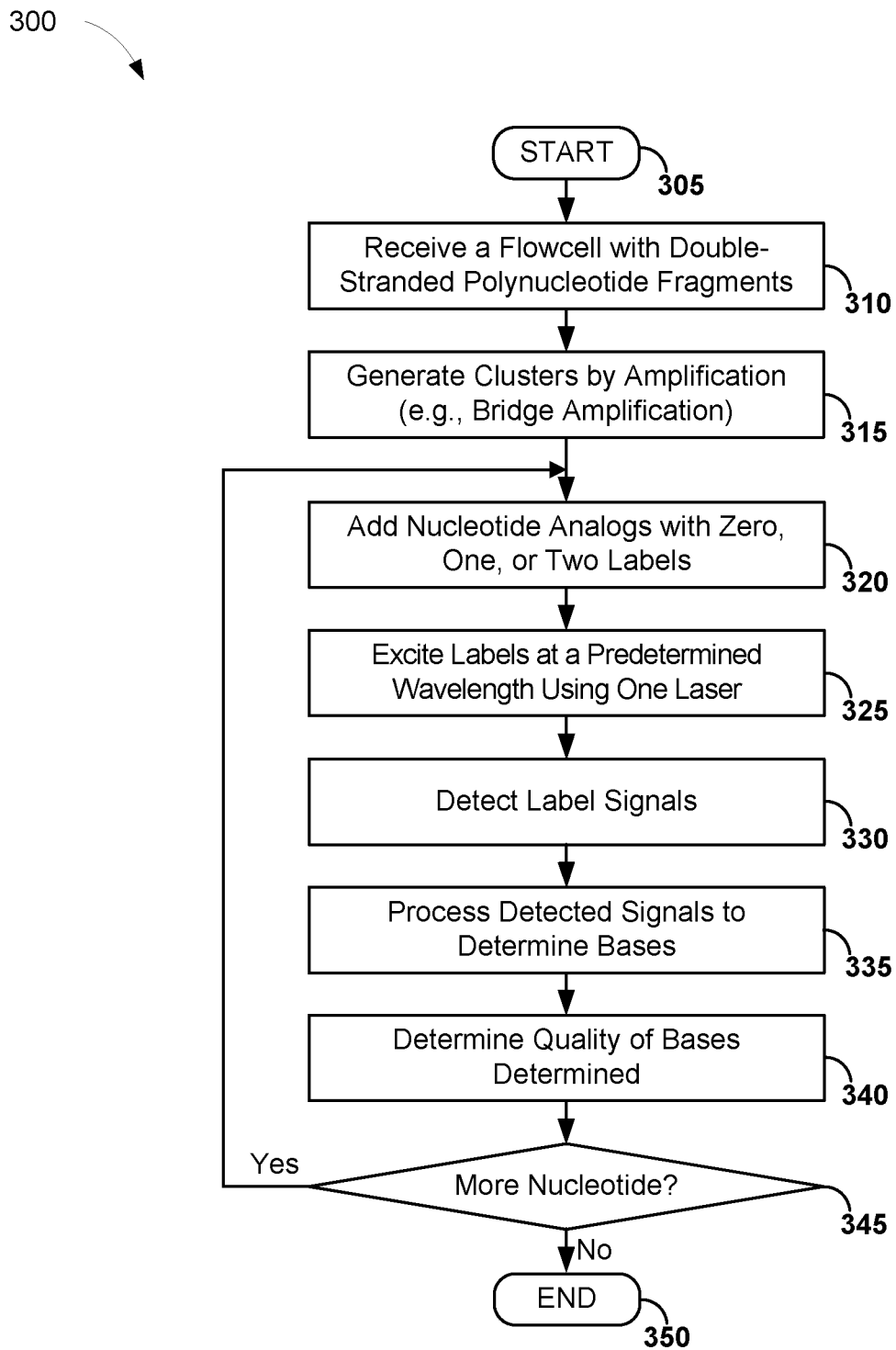
FIG. 3 is a flowchart of an example method for sequencing by synthesis.

FIG. 3 is a flowchart of an example method 300 for sequencing by synthesis utilizing the sequencing system 100. After the method 300 beings at block 305, a flowcell 114 including fragmented double-stranded polynucleotide fragments is received at block 310. The fragmented double-stranded polynucleotide fragments can be generated from a deoxyribonucleic acid (DNA) sample. The DNA sample can be from various sources for example, a biological sample, a cell sample, an environmental sample, or any combination thereof. The DNA sample can include one or more of a biological fluid, a tissue, and cells from a patient. For example, the DNA sample can be taken from, or include, blood, urine, cerebrospinal fluid, pleural fluid, amniotic fluid, semen, saliva, bone marrow, a biopsy sample, or any combination thereof.

The DNA sample can include DNA from cells of interest. The cells of interest can vary and in some embodiments express a malignant phenotype. In some embodiments, the cells of interest can include tumor cells bone marrow cells, cancer cells, stem cells endothelial cells, virally infected cells pathogenic, parasitic organism cells or any combination thereof.

The lengths of fragmented double-stranded polynucleotide fragments can range from 200 bases to 1000 bases. Once the flowcell 114 including fragmented double-stranded polynucleotide fragments are received at block 310, the method 300 proceeds to block 315, where the double-stranded polynucleotide fragments are bridge-amplified into clusters of polynucleotide fragments attached to the inside surface of one or more channels of a flowcell, for example the flowcell 114. The inside surface of the one or more channels of the flowcell can include two types of primers, for example a first primer type (P1) and a second primer type (P2) and the DNA fragments can be amplified by well-known methods.

After generating clusters within the flowcell 114, the method 300 can begin a Sequencing by Synthesis process. The Sequencing by Synthesis process can include determining the nucleotide sequence of clusters of single-stranded polynucleotide fragments. To determine the sequence of a cluster of single-stranded polynucleotide fragments with the sequence 5'-P1-F-A2R-3', primers with the sequence A2F, which are complementary of the sequence A2R, can be added and extended at block 320 with nucleotide analogs with zero, one, or two labels by a DNA polymerase to form growing primer-polynucleotides.

During each sequencing cycle, four types of nucleotide analogs can be added and incorporated onto the growing primer-polynucleotides. The four types of nucleotide analogs can have different modifications. For example, the first type of nucleotide can be an analog of deoxyguanosine triphosphate (dGTP) not conjugated with any fluorescent label. The second type of nucleotide can be an analog of deoxythymidine triphosphate (dTTP) conjugated with the first type of fluorescent label via a linker. The third type of nucleotide can be an analog of deoxycytidine triphosphate (dCTP) conjugated with the second type fluorescent label via a linker. The fourth type of nucleotide can be an analog of deoxyadenosine triphosphate (dATP) conjugated with both the first type of fluorescent label and the second type of fluorescent label via one or more linkers. The linkers may include one or more cleavage groups. Prior to the subsequent sequencing cycle, the fluorescent labels can be removed from the nucleotide analogs. For example, a linker attaching a fluorescent label to a nucleotide analog can include an azide and/or an alkoxy group, for example on the same carbon, such that the linker may be cleaved after each incorporation cycle by a phosphine reagent, thereby releasing the fluorescent label from subsequent sequencing cycles.

The nucleotide triphosphates can be reversibly blocked at the 3' position so that sequencing is controlled and no more than a single nucleotide analog can be added onto each extending primer-polynucleotide in each cycle. For example, the 3' ribose position of a nucleotide analog can include both alkoxy and azido functionalities which can be removable by cleavage with a phosphine reagent, thereby creating a nucleotide that can be further extended. After the incorporation of nucleotide analogs, the fluidics system 104 can wash the one or more channels of the flowcell 114 in order to remove any unincorporated nucleoside analogs and enzyme. Prior to the subsequent sequencing cycle, the reversible 3' blocks can be removed so that another nucleotide analog can be added onto each extending primer-polynucleotide.

At block 325, lasers such as the lasers 120 can excite the two fluorescent labels at predetermined wavelengths. At block 330, signals from the fluorescent labels can be detected. Detecting the fluorescent labels can include capturing fluorescent emissions in two fluorescent images at a first wavelength and a second wavelength by, for example, the detector 126 using two filters. The fluorescent emissions of the first fluorescent label can be at, or around, the first wavelength, and the fluorescent emissions of the second fluorescent label can be at, or around, the second wavelength. The fluorescent images can be stored for later processing offline. In some embodiments, the fluorescent images can be processed to determine the sequence of the growing primer-polynucleotides in each cluster in real-time.

In online real-time fluorescent imaging processing, the fluorescent images comprising the fluorescent signals detected can be processed at block 335, and the bases of the nucleotides incorporated can be determined. For each nucleotide base determined, a quality score can be determined at block 340. A determination can be made at decision block 345 whether to detect more nucleotides based on, for example, the quality of the signal or after a predetermined number of bases. If more nucleotides are to be detected, then nucleotide determination of the next sequencing cycle can be performed at block 320. In some embodiments, the labeled nucleotides may be added to one end of the DNA strand corresponding to a cluster. The labeled nucleotides may also be added to the other end of the DNA strand corresponding to the cluster. Reads on one end of the DNA strand are often referred to as the Read 1 set, and those reads on the other end of a DNA strand are often referred to as the Read 2 set. The sequencing technique that allows the determination of two or more reads of sequence from two places on a single polynucleotide duplex is known as paired-end (PE) sequencing. The two or more reads of sequences from the two places on the single polynucleotide duplex is referred to as Read 1 set, Read 2 set, etc. Paired-end sequencing has been described in U.S. patent application Ser. No. 14/683,580; the content of which is incorporated herein by reference in its entirety. The advantage of the paired-end approach is that there is significantly more information to be gained from sequencing two stretches from a single template than from sequencing each of two independent templates in a random fashion.

Prior to the next sequencing cycle, the fluorescent labels can be removed from the nucleotide analogs, and the reversible 3' blocks can be removed so that another nucleotide analog can be added onto each extending primer-polynucleotide. After all the fluorescent images are processed, the method 300 can terminate at block 350.

Base Calling

Figure 4:
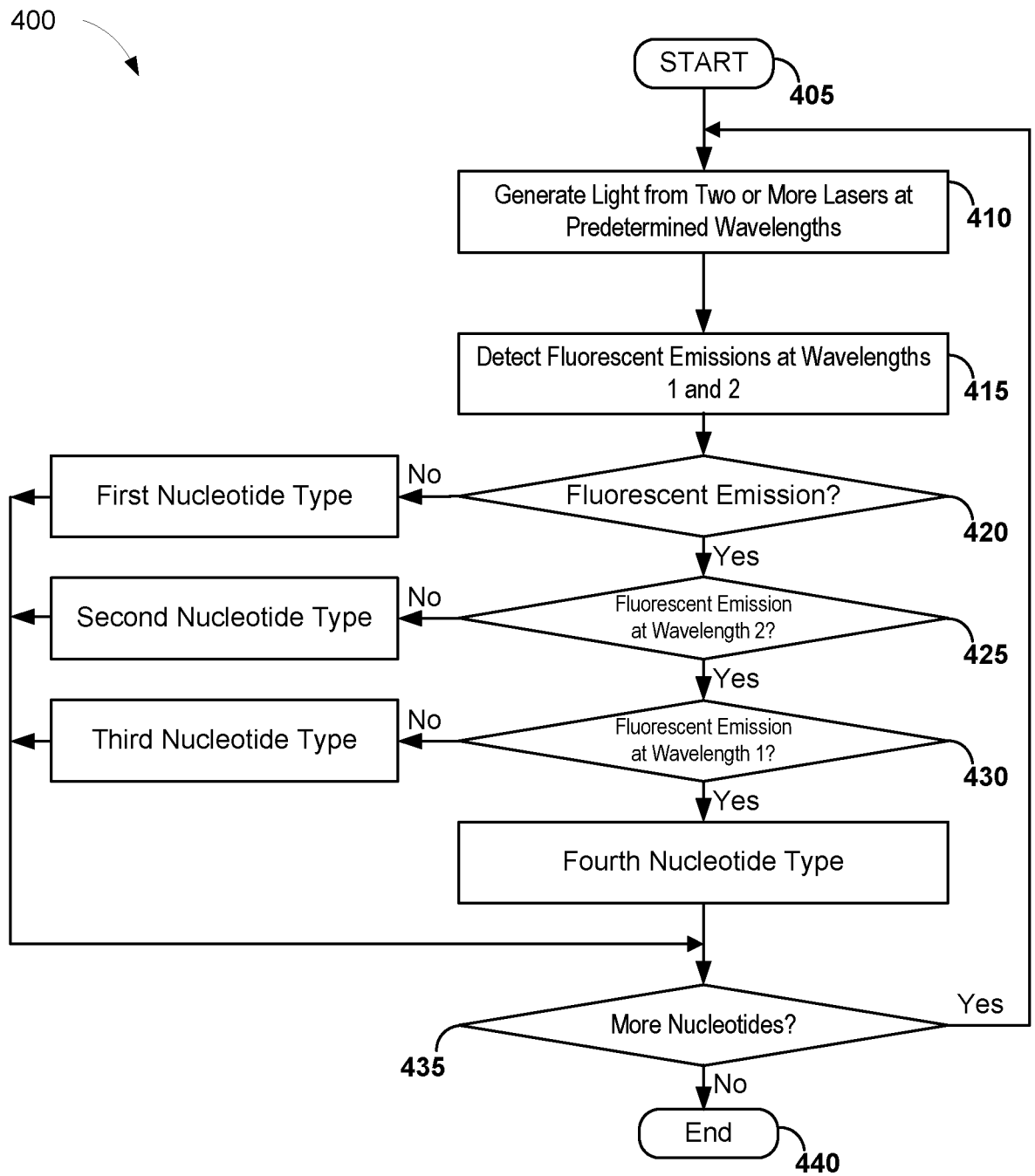
FIG. 4 is a flowchart of an example method for performing base calling.

Base calling can refer to the process of determining bases of the nucleotides incorporated into the clusters of growing primer-polynucleotides being sequenced to be guanine (G), thymine (T), cytosine (C), or adenine (A). FIG. 4 is a flowchart of an example method 400 for performing base calling utilizing the sequencing system 100. Processing detected signals at block 335 illustrated in FIG. 3 can include performing base calling of the method 400. After beginning at block 405, light of predetermined wavelengths can be generated using lasers. The light generated can shine onto nucleotide analogs at block 410. For example, the computer system 106, through its optics system interface 212 and the communication channel 108a, can cause the lasers 120 to generate light at the predetermined wavelength.

The laser-generated light can shine onto nucleotide analogs incorporated into growing primer-polynucleotides attached on inside surface of one or more channels of a flow cell, for example, the flowcell 114. The primer-polynucleotides can include clusters of single-stranded polynucleotide fragments hybridized to sequencing primers. The nucleotide analogs each can include zero, one, or two fluorescent labels. The two fluorescent labels can be a first fluorescent label and a second fluorescent label. The fluorescent labels, after being excited by the laser-generated light, can emit fluorescent emissions. For example, the first fluorescent label can produce fluorescent emissions at the first wavelength which can be captured in, for example, a first fluorescent image. The second fluorescent label can produce fluorescent emissions at the second wavelength which can be captured in, for example, a second fluorescent image.

The nucleotide analogs can include a first type of nucleotide, a second type of nucleotide, a third type of nucleotide, and a fourth type of nucleotide. The first type of nucleotide, for example an analog of deoxyguanosine triphosphate (dGTP), is not conjugated to the first fluorescent label or the second fluorescent label. The second type of nucleotide, for example an analog of deoxythymidine triphosphate (dTTP), can be conjugated with the first type of fluorescent label, and not the second type of fluorescent label. The third type of nucleotide, for example an analog of deoxycytidine triphosphate (dCTP), can be conjugated with the second type fluorescent label, and not the first type of fluorescent label. The fourth type of nucleotide, for example an analog of deoxyadenosine triphosphate (dATP), can be conjugated with both the first type of fluorescent label and the second type of fluorescent label.

At block 415, fluorescent emissions of the nucleotide analogs at the first wavelength and the second wavelength can be detected using at least one detector. For example, the detector 126 can capture two fluorescent images, a first fluorescent image at the first wavelength and a second fluorescent image at the second wavelength. After receiving the two fluorescent images from the optics system 102, the nucleic base determiner 216 can determine the presence or the absence of fluorescent emissions in the two fluorescent images.

Because the first type of nucleotide is not conjugated to the first fluorescent label or the second fluorescent label, the first type of nucleotide can produce no, or minimal, fluorescent emission at the first wavelength or at the second wavelength. At decision block 420, if no fluorescent emission is detected, the nucleotide can be determined to be the first type of nucleotide, for example dGTP. If any or more than minimal fluorescent emission is detected, the method 400 can proceed to decision block 425.

Because the second type of nucleotide is conjugated with the first type of fluorescent label, and not the second type of fluorescent label, the second type of nucleotide can produce fluorescent emissions at the first wavelength and no, or minimal, fluorescent emission at the second wavelength. At decision block 425, if no fluorescent emission at the second wavelength is detected in the second fluorescent image, and from decision block 420, fluorescent emissions at the first wavelength are detected in the first fluorescent image, then the nucleotide can be determined to be the second type of nucleotide, for example dTTP. If fluorescent emissions are detected at the second wavelength, the method 400 can proceed to decision block 430.

Because the third type of nucleotide is conjugated with the second type fluorescent label, and not the first type of fluorescent label, the third type of nucleotide can produce fluorescent emissions at the second wavelength and no, or minimal, fluorescent emission at the first wavelength. At decision block 430, if no fluorescent emission at the first wavelength is detected in the first fluorescent image, and from decision block 425, fluorescent emissions at the second wavelength are detected in the second fluorescent image, then the nucleotide can be determined to be the third type of nucleotide, for example dCTP.

Because the fourth type of nucleotide is conjugated with both the first type of fluorescent label and the second type of fluorescent label, the fourth type of nucleotide can produce fluorescent emissions at the first wavelength or the second wavelength. At decision block 430, if fluorescent emissions are detected at the first wavelength in the first fluorescent image, and from decision block 425, fluorescent emissions can be detected at the second wavelength in the second fluorescent image, then the nucleotide can be determined to be the fourth type of nucleotide, for example dATP.

The flowcell 114 can include clusters of growing primer-polynucleotides to be sequenced. At decision block 435, if there is at least one more cluster with fluorescent emissions to be processed for a given sequencing cycle, the method 400 can continue at block 410. If no more cluster of single-stranded polynucleotide is to be processed, the method 400 can end at block 440.

Sequencing Methods

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

"Sequencing-by-synthesis ("SBS") techniques" generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

Iterative Alignment and Variant Calling

Figure 5A:
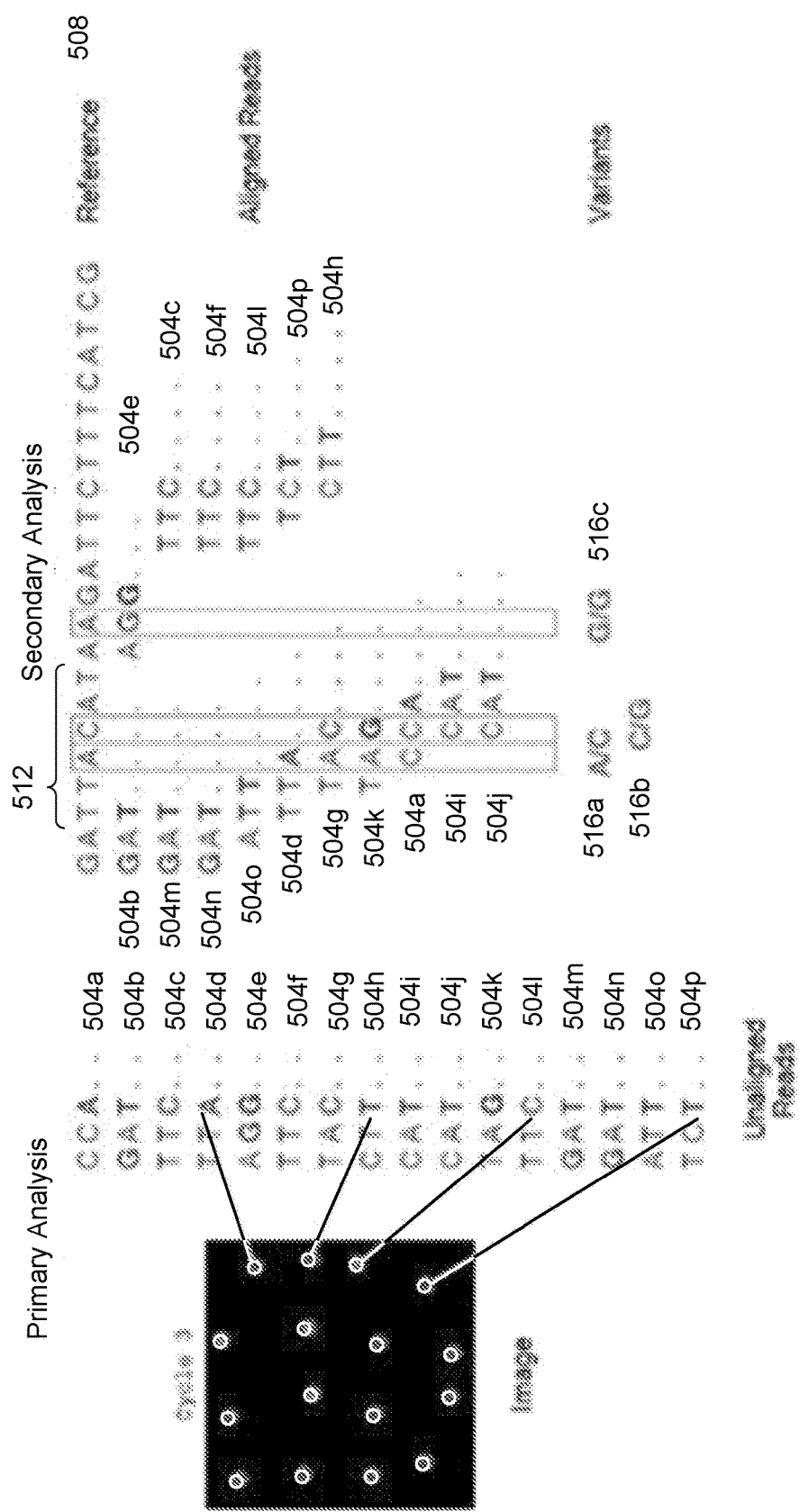
FIGS. 5A and 5B show example iterative alignments and variant calling.
Figure 5B:
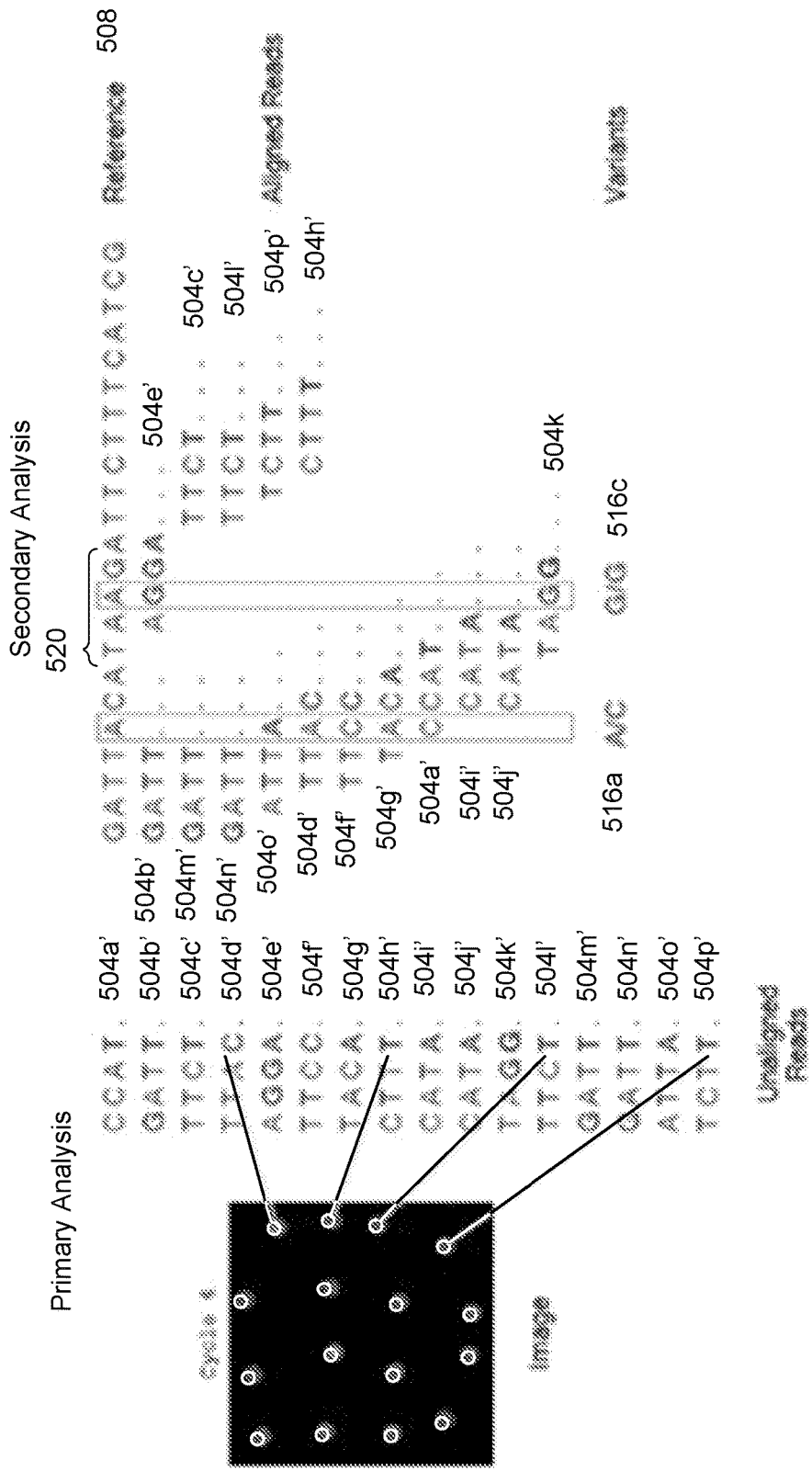

FIGS. 5A and 5B show an example iterative alignment and variant calling process according to one embodiment. After a certain number of minimum sequencing cycles have been imaged, real-time primary analyses can be performed in order to determine the base calls and quality scores for each unaligned read. In FIG. 5A, the minimum number of sequencing cycles shown is three. In some embodiments, the minimum sequencing cycles can be 16, 32, or more cycles. Base calling and quality score determination are illustrated above with reference to FIG. 3. Each read can be aligned to the reference sequence with the most likely alignment being chosen, and then the reads can be stacked in a pile-up and variant calling can be performed.

In FIG. 5A, the primary analyses includes determining unaligned sequence reads, such as CCA 504a, TTA 504d, and TAG 504k, from 16 clusters shown on the flowcell. Under the Primary Analysis heading, each cluster is represented as a row of letters, with each letter representing a sequenced polynucleotide. Once the minimum number of cycles have been sequenced, e.g. 3 cycles, secondary analyses can include aligning the 16 sequence reads to a reference sequence (GATTACATAAGATTCTTTCATCG 508) shown under the Secondary Analysis heading in FIG. 5A. In the Secondary Analysis diagram, the sequences aligned under the reference sequence constitute a pile-up of polynucleotides. As an example, the sequence reads CCA 504a (row 1 under the "Primary Analysis" heading), TTA 504d (row 4), and TAG 504k (row 11) can be aligned to sequences ACA, TTA, and TAC, respectively, within the TTACAT 512 subsequence of the reference sequence 508, with one, zero, and one mismatch, respectively. Thus, the third position of the TTACAT 512 subsequence can be determined to be a C 516a instead of an A in the reference sequence 508 with some probability of correctness, and the fourth position of the TTACAT 512 subsequence can be determined to be a G 516b instead of a C in the reference sequence with some probability of correctness. Other variants of the reference sequence can be similarly determined.

As new sequencing cycles are performed and base calls determined, the alignment probabilities can be refined, and the read alignments may shift to a new most-likely alignment. This shift would trigger new variant calling to be performed in the affected regions. In FIG. 5B, after a fourth sequencing cycle, the sequencing reads CCA 504a, TTA 504d, and TAG 504k from the third sequencing cycle become CCAT 504a' (row 1 under the "Primary Analysis" heading), TTAC 504d' (row 4), and TAGG 504k' (row 11) respectively. The sequence reads CCAT 504a' and TTAC 504d' can still be aligned to the TTACAT 512 subsequence of the reference sequence 508, with one and zero mismatch respectively. For sequence reads CCAT 504a' and TTAC 504d', the alignment position does not change between the iteration shown in FIG. 5A and the iteration shown in FIG. 5B; the third position of the TTACAT 512 subsequence can be determined to be a C 516a instead of an A in the reference sequence. To align the read TAGG 504k' to the TTACAT 512 subsequence requires two mismatches. However, the sequence read TAGG 504k' can be aligned to TAAG 520 of the reference sequence 508 with higher probability, since this alignment has only one mismatch, The examples of FIG. 5A and FIG. 5B show that alignment positions may shift as the sequencing run proceeds, and variant calling may improve.

In some embodiments, aligning sequence reads to a reference sequence comprises keeping a list of most likely alignments as leaves on a node for each sequence read. Each leaf can have an associated probability. Leaves with probabilities that drop below some threshold can be trimmed.

Real-Time Secondary Analyses

Figure 6:
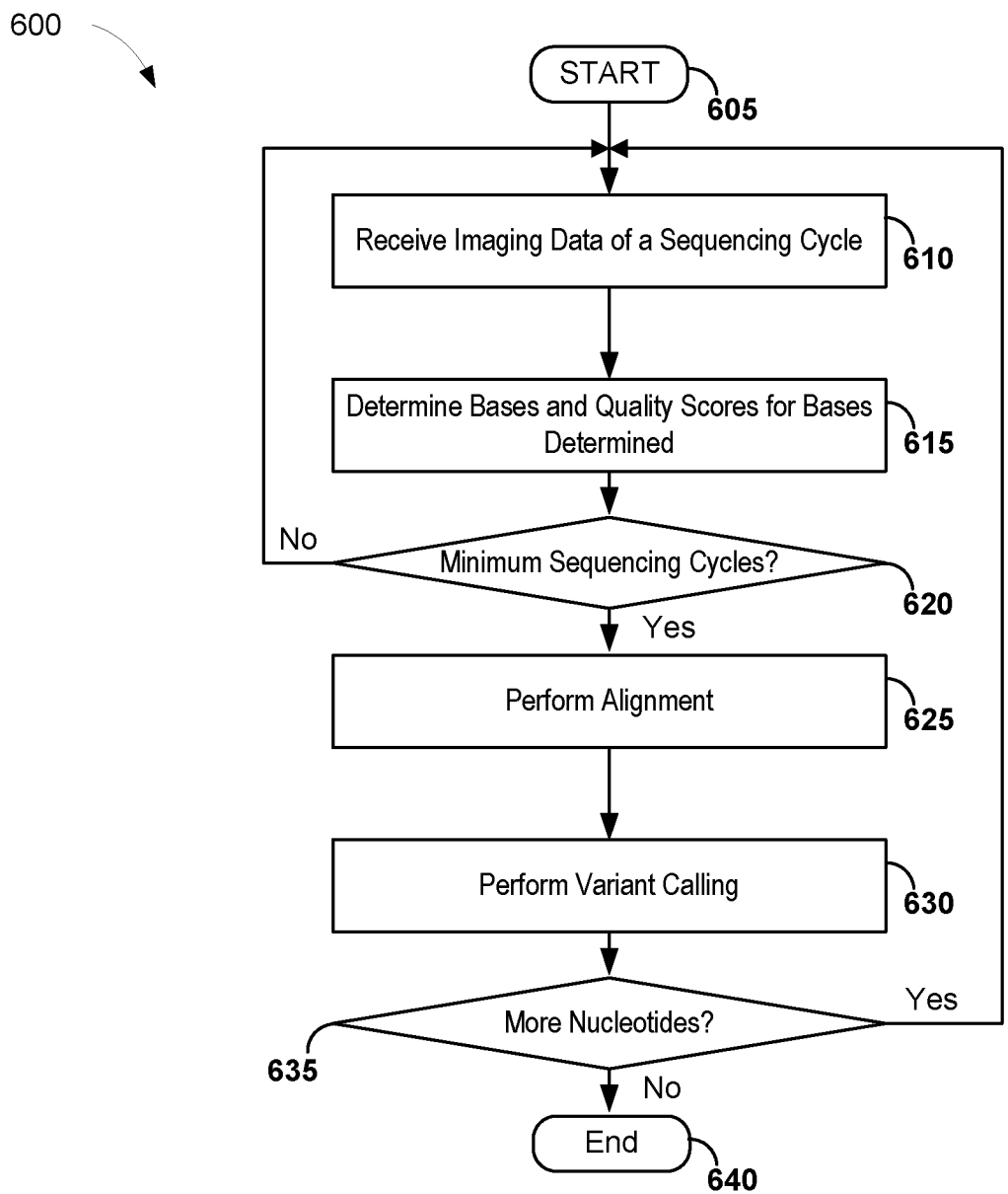
FIG. 6 is a flowchart of an example method for performing a real-time secondary sequence analysis.

FIG. 6 is a flowchart of an example method 600 for performing a real-time secondary sequence analysis. After the method 600 starts at block 605, imaging data of a sequencing cycle can be received at block 610. For example, the computer system 106 can receive the imaging data from the detector 126. At block 615, bases can be determined and quality scores of the bases can be determined. Generating imaging data and determining bases and quality of bases determined are illustrated above with reference to FIGS. 3-4. After each sequencing cycle, the lengths of sequencing reads become one nucleotide longer. For example, after the 31st sequencing cycle, the sequencing reads are 31 nucleotides in length, and after the 32nd sequencing cycle, the sequencing reads become one nucleotide longer to 32 nucleotides in length.

At decision block 620, whether a certain number of minimum sequencing cycles have been performed can be determined. The minimum sequencing cycles can be 16, 32, or more cycles. If the number of sequencing cycles performed is lower than the minimum sequencing cycles required, the method 600 proceeds to block 610. If the number of sequencing cycles performed is at least the minimum sequencing cycles required, the method 600 proceeds to block 625.

At block 625, the sequence reads determined can be aligned to a reference sequence. The method 600 can utilize different alignment methods in different implementations. Non limiting examples of alignment methods include global alignments (such as Needleman-Wunsch algorithm), local alignments, dynamic programming (such as Smith-Waterman algorithm), heuristic algorithms or probabilistic methods, progressive methods, iterative methods, motif finding or profile analysis, genetic algorithms, simulated annealing, pairwise alignments, multiple sequence alignments.

At block 630, variants can be determined. An initial variant may be called only after a predetermined variant threshold is reached. The variant threshold may be important due to possible PCR or sequencing errors. The variant threshold can be based on the alignment of a base to a position of the reference sequence that is different from the base at the corresponding position of the reference sequence.

In FIG. 5A, the variant threshold is one observation. Thus, the third position of TTACAT can be determined to be a C instead of an A in the reference sequence. If the variant threshold is two or more, the C variant will not be called at block 630 at the particular sequencing cycle. In FIG. 5B, the third position of TTACAT can be determined to be a C instead of an A in the reference sequence if the variant threshold is at most two observations. In some embodiments, the variant threshold can be a percentage of all bases aligned to a particular position of the reference sequence, such as 1%, 5%, 10%, 25%, 50%, or more. As described in further details below, most likely alignments can be stored as leaves on a node for each sequence read. Each leaf can have an associated probability. Leaves with probabilities that drop below some threshold can be trimmed. Thus, variants called for a nucleotide position on the reference sequence may be refined or may drop off during subsequent cycles.

A determination can be made at decision block 635 whether there are more nucleotides to be read or all sequencing cycles are complete. This determination can be based on, for example, the quality of the signal or after a predetermined number of bases. If there are more nucleotides to be read and not all sequencing cycles are complete, then the method 600 proceeds to block 610, where sequencing data can be generated for the next sequencing cycle. If there are no more nucleotides to be read and all sequencing cycles are complete, the method 600 ends at block 650.

In some embodiments, blocks 625 and 630 and blocks 610 and 615 can be performed in parallel after the minimum number of sequencing cycles have been performed. For example, after 32 sequencing cycles are performed, the method can proceed to block 625 to perform alignment of sequence reads that are 32 nucleotides in length. While the method 600 performs alignment at block 625 and variant calling at block 630, the next sequencing cycle (i.e., the 33rd sequencing cycle) can be performed. Thus, variants can be determined at block 630 prior to completion of the 33rd sequencing cycle. And the method 600 can enable alignment and variant calling in real time (or with zero or low latency) while sequencing cycles are performed. Furthermore, the variants called during earlier sequencing cycles may be refined during subsequent cycles. Thus, variant calling illustrated in FIG. 6 can be an iterative process. For example, the variant called after the 32nd sequencing cycle or during the 33rd sequencing cycle may be an initial variant called. During subsequent sequencing cycles, the variant called may be refined (including that a variant previously called for a particular nucleotide position is no longer called and drops off). As another example, as shown in FIGS. 5A and 5B, a variant for the fourth position of TTACAT was called to be a G after the third cycle, while no variant for the position was called after the fourth position.

In another embodiment, the sequencing process may be terminated prior to the time that all sequencing cycles are complete. For example, if a particular target variant is identified prior to the completion of all the sequencing cycles, the sequencing process may terminate. This allows the system to save costs on reagents and provide the desired result earlier than systems that need to complete all cycles before a target variant call is made.

In some embodiments, the alignment may not be performed at block 625 and variants called at block 630 every sequencing cycle. For example, alignments may be performed and variants called every nth sequencing cycle, where n is 1, 2, 3, 4, 5, 10, 20, or more sequencing cycles. In some embodiments, the frequency of the alignment performed at block 625 and variants called at block 630 may be based on the number of variants called in the previous sequencing cycle. For example, if a large number of variants are called in one sequencing cycle, alignments and variant calling may be performed more frequently (e.g., the next cycle) or less frequently. As another example, if no variant or no new variant has been called in one sequencing cycle, alignments and variant calling may be performed more frequently or less frequently (e.g., not the next cycle).

In some embodiments, the variant calling at block 630 may be performed selectively for a region of the reference sequence. The portion of the reference sequence being aligned may be different in different implementations. For example, variant calling may be performed selectively for a region of the reference sequence where the alignment of the sequence reads to the reference sequence has changed during a previous sequencing cycle (e.g., the immediate prior sequencing cycle). As another example, the region of the reference sequence being aligned may be determined based on known single nucleotide polymorphism (SNP) locations.

In some embodiments, the method 600 for performing a real-time secondary sequence analysis can be based on a tree structure for each read. The root of the tree can be labelled with a "$", indicating the start of the sequence. The child nodes of the root correspond to the four possible base calls: 'A', 'C', 'G' and 'T'. Each node in the tree can have three variables associated with it: the total number of differences of the sequence of the current branch leading from the root to that node (referred to as sequence S), with the bases from the current read (referred to as sequence W), and then the start and stop indices in the Burrows-Wheeler Transform (BWT) of the reference sequence for all positions in the reference that match the sequence S. An important property of the BWT is that all rows that have a common starting sequence are guaranteed to be consecutive in the transform, and so rather than keeping a list of individual indices into the reference that match the sequence S, it is sufficient to track the start and stop indices. This is valuable in the case of mapping reads to the human reference genome because there are very many repetitive regions.

Each child node of the root would then also have 4 children of its own, also corresponding to the four possible bases 'A', 'C', 'G' and 'T'. Again, the number of differences with the sequence of the current read, W, can be tracked. For example, if the read of the first two cycles were 'C' and then 'T', the read can have a path through the tree defined by Root→C→T. Thus, the total accumulated differences would be zero for the last T node. In contrast, for the path defined by Root→A→G, the total accumulated differences at the G node would be 2, because neither the A nor the G match the corresponding cycle in the current read.

In some embodiments, a limit on the number of differences with the reference that is acceptable can be defined. Once that limit is reached, that branch is dead and will no longer be analyzed it in subsequent cycles. The BWT transform, with appropriate indices, can be used to perform the calculations necessary at each node in constant, O(1), time. The amount of memory required for the computation, and the number of nodes in the tree, are influenced by the total number of allowable errors threshold. In some embodiments, support for small insertions and deletions can be implemented In some embodiments, more complex rearrangements would be handled through multiple seeds. That is, if a particular read is found to not match anywhere, the process may start again at some later cycles, with the expectation that the other part of the read would map somewhere. All of these reads can be tracked, and a more complex analysis (e.g., a dynamic programming method like the Smith-Waterman algorithm) can be performed when there are computing powers available.

Alternative Embodiment

Additional embodiments are systems and methods for secondary analysis that include iterative processing of sequencing reads. Secondary analyses can encompass both alignment of sequence reads to a reference sequence (e.g., the human reference genome sequence) and utilization of this alignment to detect differences between a sample and the reference, such as variant detection and calling. In one implementation, alignment and variant call results can be obtained before the sequencer has finished running. For example, these results may be provided at time intervals dependent on the available computing resources. This can be accomplished by extending intermediate alignment results from a prior iteration with alignment results from the current iteration. The alignment results from the current iteration are generated by comparing the newly sequenced bases of the current iteration with the bases from the reference sequence at the previously aligned position. The results of the comparison are combined with the alignment results from the prior iteration, and the combined output is stored for the next iteration.

Figure 7A:
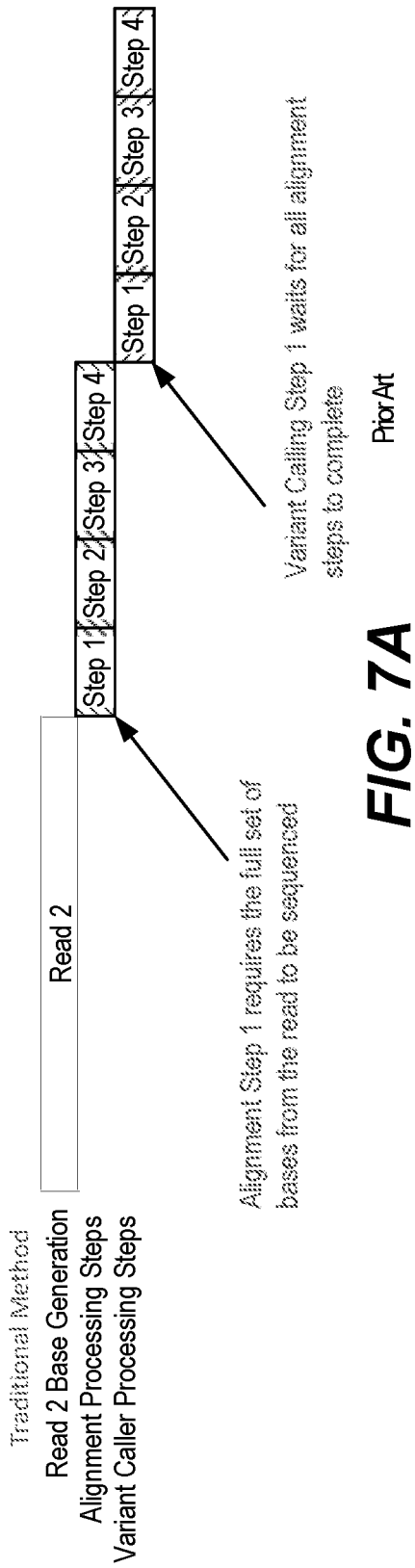
FIGS. 7A and 7B are schematic illustrations comparing a traditional method of secondary analysis (FIG. 7A) to an iterative method of secondary analysis (FIG. 7B).
Figure 7B:
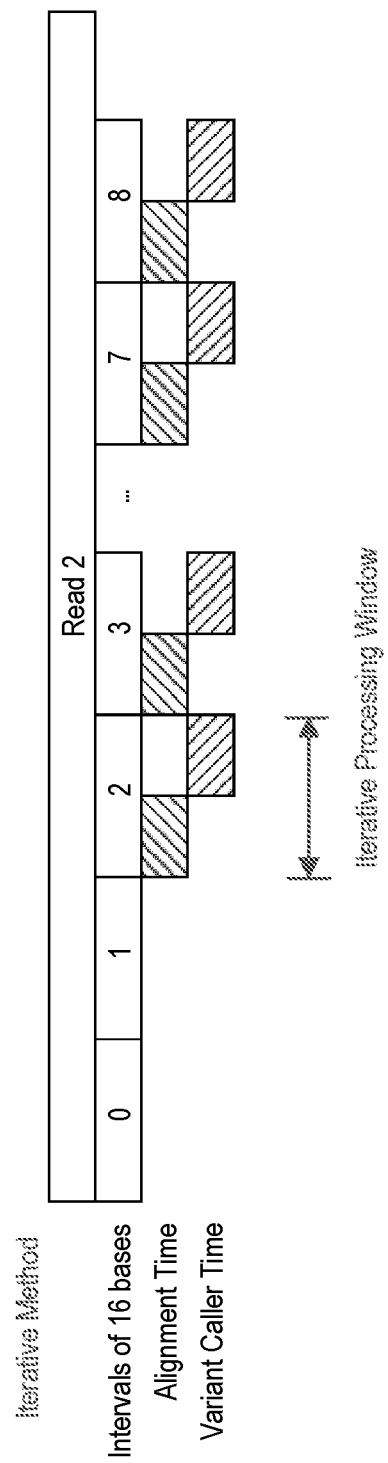

FIGS. 7A and 7B are schematic illustrations comparing a traditional method of secondary analysis (FIG. 7A) to the secondary analysis of an embodiment of the present disclosure (FIG. 7B). FIG. 7A illustrates that for a traditional method of secondary analysis, the alignment does not proceed until the full set of bases in the read are sequenced. The alignment process can include multiple alignment processing steps. The first alignment processing step waits for the full set of sequenced bases in the read to be available. After the alignment process is complete, the variant caller process, which includes multiple variant caller processing steps, can begin. The first variant caller processing step waits for the full set of alignment data to be available.

Figure 8:
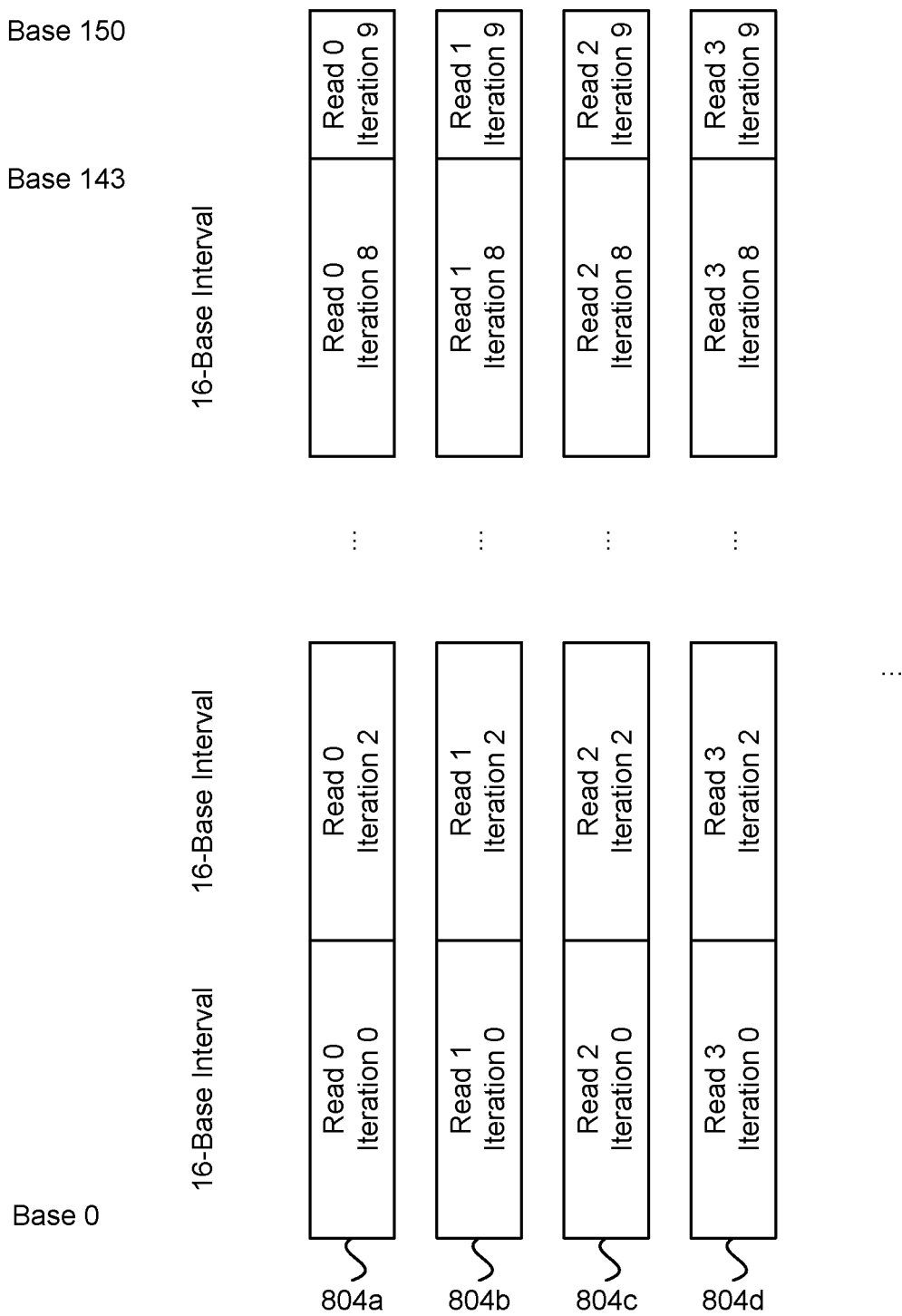
FIG. 8 is a schematic illustration of read generation at 16-base interval.

FIG. 7B illustrates an iterative method of secondary analysis according to one embodiment of the present disclosure. As shown, alignment and variant calling run in real time and generate interim results. Processing can be scheduled at fixed intervals. The fixed intervals can include the arrival of a subsequence of N bases, where N is a positive integer, such as 16. For example, processing can occur at intervals of 16 bases. As another example, processing can occur at intervals of 1, 2, 4, 8, 16, 32, 64, 128, 151, or more bases. In one implementation, processing can occur at intervals of any number between 1 and 152, most preferably at intervals of 16+/−8. In one embodiment, the intervals can change from one iteration to another iteration. A sequencing system, such as the sequencing system 100 in FIG. 1, can generate sequence reads at intervals of 16 bases as illustrated in FIG. 8. Alternatively, the number of bases in each processing interval may be different. For example, the first interval can be processed after 16 bases are sequenced, and the second iteration can be processed after 18 bases are sequenced. The number of bases in the iteration may be as low as 1 or as high as the number of bases in the read.

The process described in FIG. 7B can be applied to the Read 1 set or the Read 2 set when a paired end sequencing technique is used. Additionally, information captured when processing the Read 1 set may be applied to the Read 2 set. For example, it would be possible to execute the alignment step using conventional methods during or after the Read 1 set is sequenced, and this information can be used to process the Read 2 set as the Read 2 polynucleotides are sequenced.

Referring now to FIG. 8, multiple reads 804a-804d of single-stranded polynucleotides may be generated from a sequencing instrument. These single-stranded polynucleotides can be 151 bases in length, referred to as base 0 to base 150. The sequences of these single-stranded polynucleotides can be determined with sequencing by synthesis described above. After iteration 0 (the first iteration) of 16 sequencing cycles, 16 bases of sequence reads are determined by a sequencing system. For example, sequence reads of Base 0 to Base 15 are generated for Read 0 (804*a*) and sequence reads of Base 0 to Base 15 are determined for Read 1 (804*b*), etc. After iteration 1 (the second iteration) of another 16 sequencing cycles, 16 additional bases of sequences are determined for each read. For example, Base 16 to Base 31 are generated for Read 0 (804*a*). The sequencing system can continue to generate reads at 16-base interval until the sequence reads of Base 128 to Base 143 of each cluster are generated at iteration 8. The sequencing system can generate reads of Base 144 to Base 151 of each cluster at iteration 9 (the last iteration). In an alternative embodiment, the number of bases generated at each iteration may be different, with the number of bases per iteration determined by the available computing resources. For example, the first processing interval may consist of 16 bases, while the second processing interval may consist of 18 bases. The smallest number of bases in a processing interval is one, and the largest number of bases in a processing interval is equal to the length of the read.

Referring to FIG. 7B, alignment can occur at intervals of 16 bases as illustrated. Variant calling can occur at intervals of 16 after alignment is complete. For example, a sequencing system for real-time secondary analysis may output 16 bases of sequence reads every 1.3 hours. For read-time secondary analysis, the total time required for performing alignment and variant calling should be within 1.3 hours such that a user can have access to the variant calls made prior to the next 16 bases of sequence reads are available.

In one embodiment, processing can occur continuously as fast as possible on the available computer resources, with no fixed iteration steps. The analysis can self-adjust and will be as close to the sequencing progress as possible. Alignments and variant calling results can be generated on demand at any time.

Alternative Embodiment—Alignment

Figure 9A:
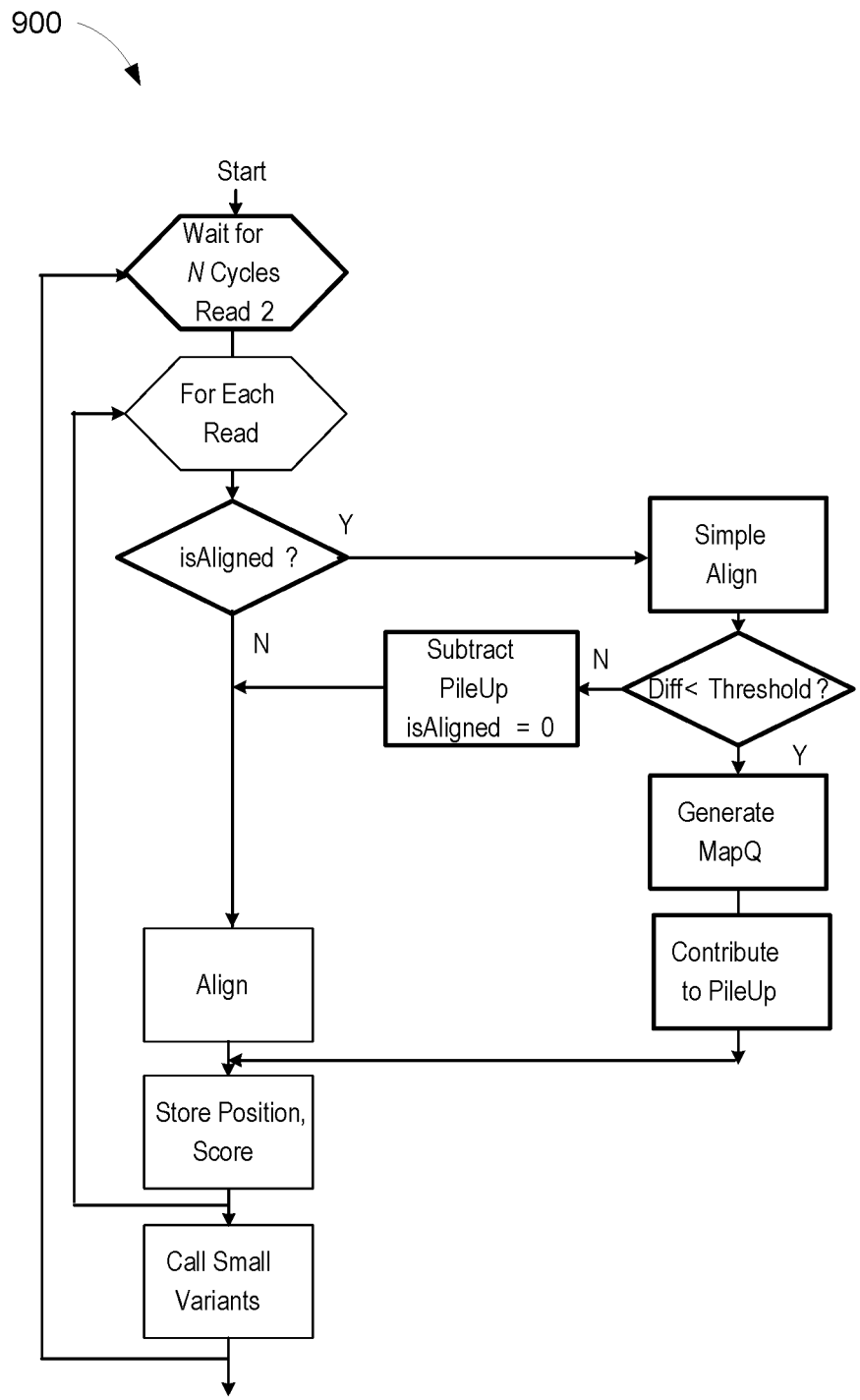
FIG. 9A is a flowchart of an example method for performing a real-time secondary analysis.
Figure 9A:
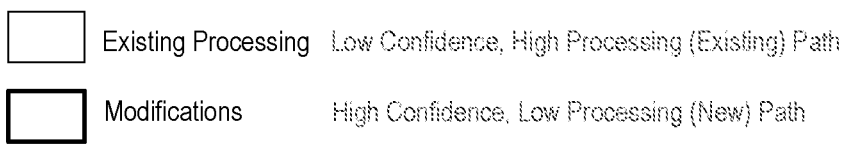

FIG. 9A is a flowchart of an example method 900 for performing a real-time secondary analysis. The method 900 includes two paths: a low confidence, high computation processing path of a traditional secondary analysis method and a high confidence, low computation processing path according to one embodiment of the present disclosure. The low confidence, high processing path and the high confidence, low processing path are referred to herein as the blue path and the yellow path respectively.

The low confidence, high computation processing path can include the sequence alignment of each read to a reference sequence. For this path, all bases from the available iterations of the read are used to align the read to the reference sequence. For example, if iteration 0 and iteration 1 each consist of 16 bases, then 32 bases will be processed by the aligner. One of a number of conventional alignment techniques may be used for the low confidence, high computation path. Once sequence alignment is complete, the mapping and alignment positions can be stored and scored. After all reads are aligned, variants can be called.

The method 900 improves upon the traditional method of secondary analysis by adding a high confidence, low computation processing path. At iteration 0, the method 900 waits for a number of sequencing cycles to be complete to generate a number of bases of each read. For example, the method 900 can wait for 16 cycles of sequencing to complete to generate 16 bases of each read. During iteration 0, the 16 bases of each read are analyzed and processed following the low confidence, high computation processing path. The traditional method is referred to herein as the blue path. During iteration 1 and any subsequent iteration, the next 16 bases of each read are analyzed following either the low confidence, high computation processing path or the high confidence, low computation processing path. If the read was aligned with sufficient confidence in the immediate prior iteration, the 16 bases of the current iteration are analyzed following the high confidence, low computation processing path. Otherwise, the 16 bases of the current iteration are analyzed following the high confidence, low computation processing path.

If the read was aligned with sufficient confidence in the immediate prior iteration, the 16 bases of the current iteration are aligned to the next 16 bases of the reference sequence. This alignment is referred to herein as simple alignment, which requires less processing compared to conventional sequence alignment. Instead of sequence alignment to the entire reference sequence, the number of mismatches between the 16 bases of the current iteration and the next 16 bases of the reference sequence can be determined. If the number of mismatches is above a threshold, processing of the 16 bases can return to the low confidence, high computation processing path. An isAligned variable can be set to 0 or false upon returning to the low confidence, high processing path. The number of mismatches can be determined with respect to the 16 bases of the current iteration or all bases of the current iteration and prior iteration(s).

If the number of mismatches is below a threshold, processing of the 16 bases can stay in the high confidence, low computation processing path, and the alignment result of the particular read can be stored. Alternative metrics may be formulated to determine if the isAligned variable is set to 0 or False. For example, if the number of mismatches is below the threshold, the (MAPping Quality) MapQ score can be calculated. The MapQ score can equal to $-10 \log_{10} \Pr\{\text{mapping position is wrong}\}$, rounded to the nearest integer. So if the probability of correctly mapping some random read was 0.99, then the MapQ score should be 20 (i.e. $\log_{10}$ of $0.01*-10$). If the probability of a correct match increased to 0.999, the MapQ score would increase to 30. Conversely, as the probability of a correct match tends towards zero, so does the MapQ score.

When the processing of the 16 bases stays in the high confidence, low computation processing path, the read can contribute to the pile-up (when multiple reads are aligned to similar locations of the reference sequence such that these reads "pileup" on top of one another on the reference sequence). When the processing of the 16 bases returns to the low confidence, high computation processing path, the read can be removed from pile-up. In one embodiment, a read is processed in the low confidence, high computation processing path only if the number of candidates, the total number of sequence alignment locations, is lower than a threshold, such as 1000. The result of alignment when a read is processed is stored.

Figure 9B:
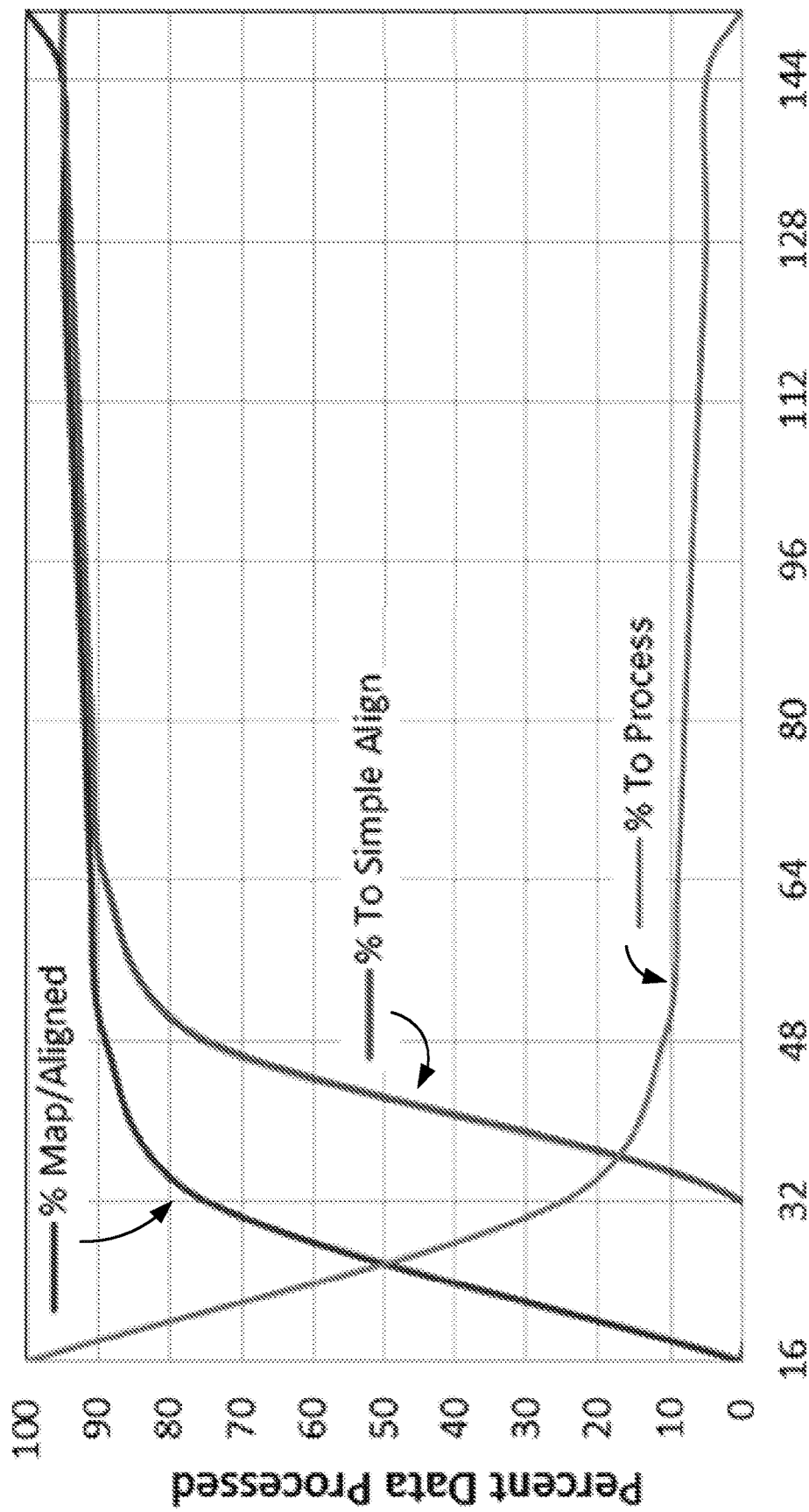
FIG. 9B is a predicted line graph showing data processed per K-Mer.

FIG. 9B is a conceptual plot of the amount of data processed by the two processing paths using method 900 shown in FIG. 9A. After 16 sequencing cycles, 16 bases of each read are generated by a sequencing system. The reads are all processed in the low confidence, high computation processing path during iteration 0. After 32 sequencing cycles, around 75% of the candidates are considered aligned after iteration 1. These candidates are processed in the high confidence, low computation processing path during iteration 2. After iteration 2, around 90% of the candidates are considered aligned and are processed in the high confidence, low computation processing path during iteration 3. Less computing and processing were required when reads are processed in the high confidence, low computation processing path because only simple alignments are required. Because a lot of data is processed in the high confidence, low computation processing path and less processing is required in this path, the total time required was lower than if the reads are only processed in the low confidence, high computation processing path. Thus, alignment and variant call results can be obtained before the sequencer has finished running. These results can be provided to a user at time intervals dependent on the available computing resources. Accordingly, the method 900 can perform secondary analyses in a time efficient manner to enable real-time secondary analyses.

Figure 9C:
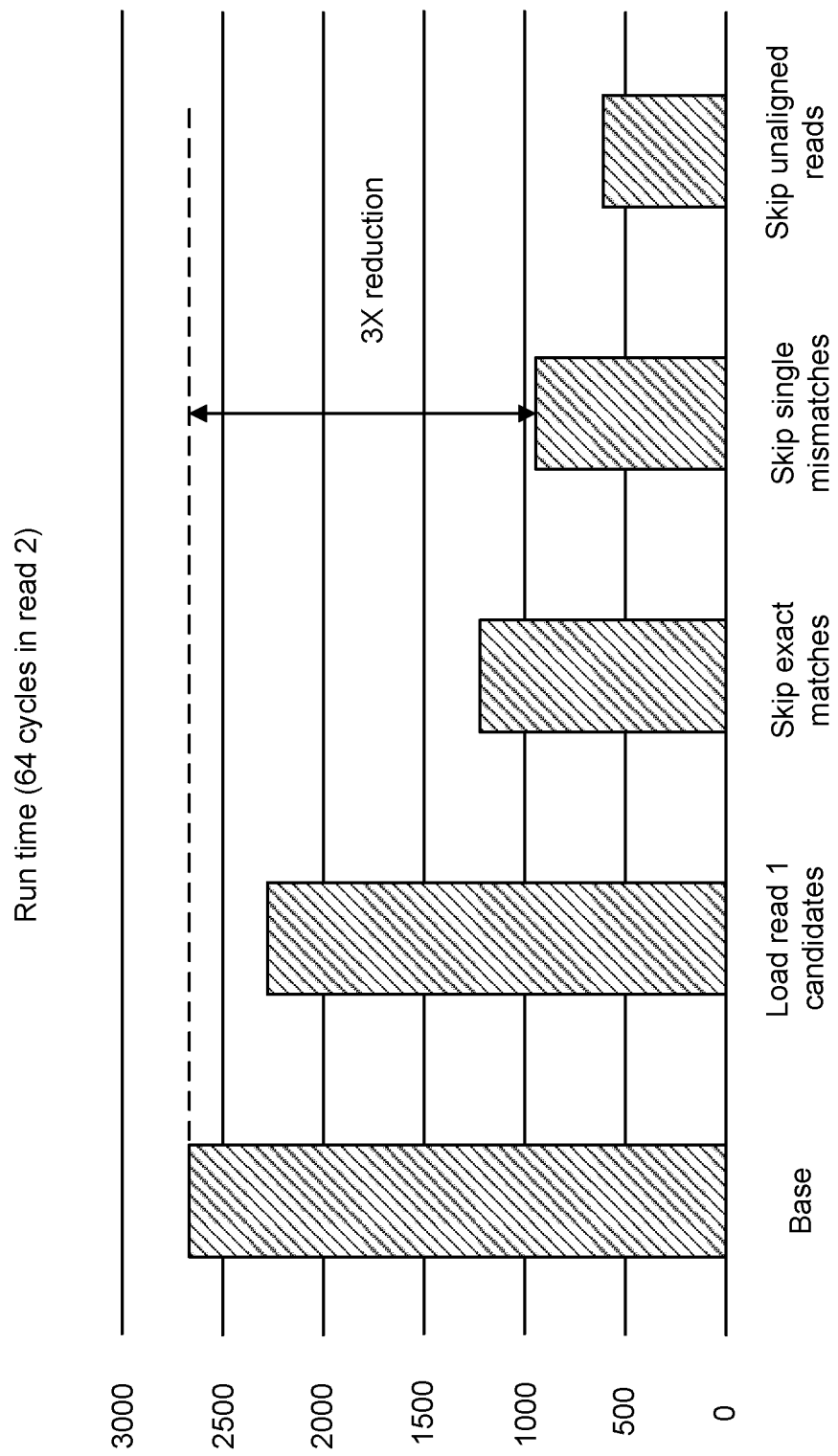
FIG. 9C is a bar chart showing run times.
Figure 10:
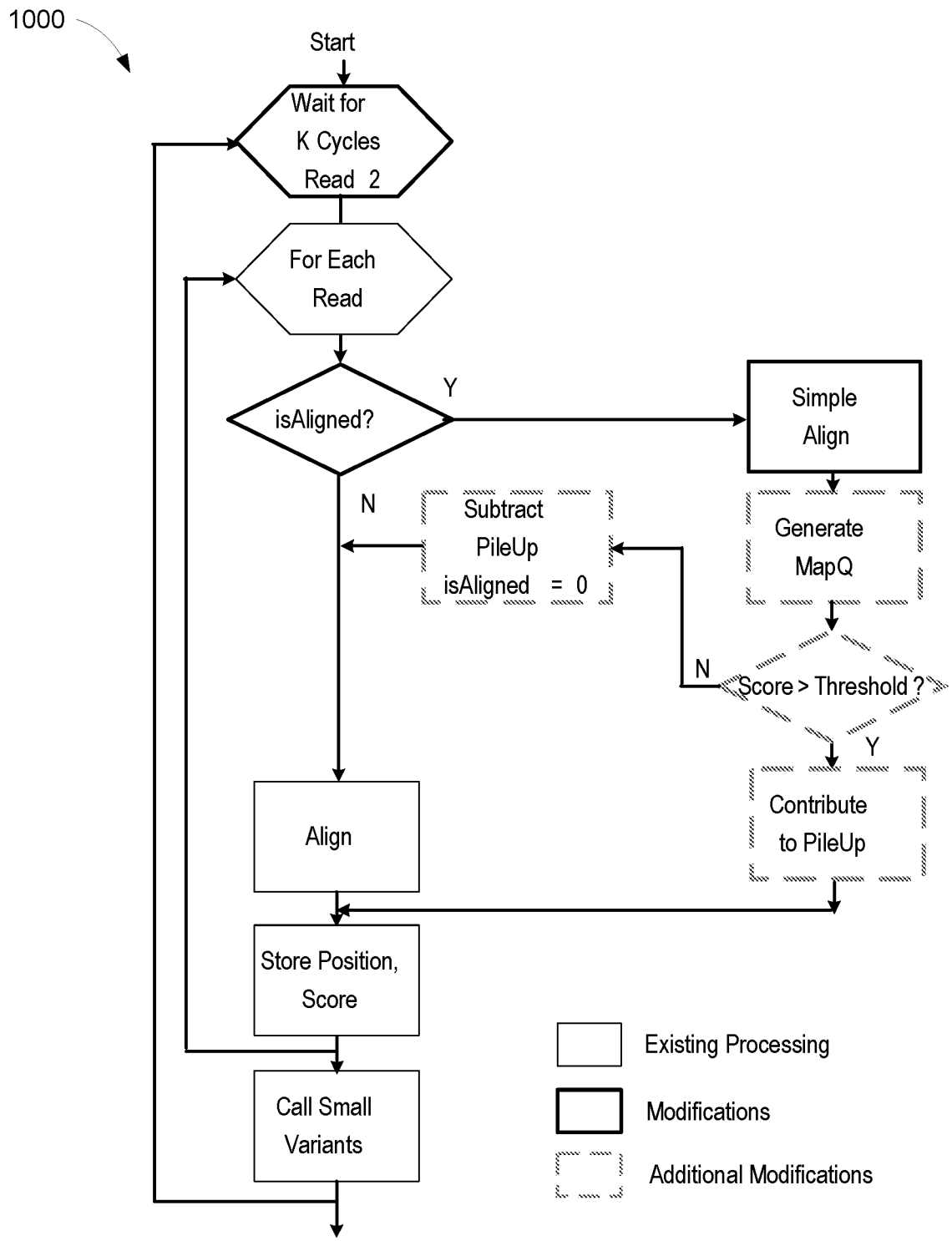
FIG. 10 is another flowchart of an example method for performing a real-time secondary analysis.

FIG. 9C shows the predicted run-time improvement of the aligner described in FIG. 10. The "Base" data is generated using only of the "Existing Processing" (conventional or blue path) in FIG. 10. The "Load Read 1" data shows the reduced processing cycles when data from the Read 1 set is aligned, pre-stored, and then utilized to accelerate processing of the data in the Read 2 set. The method 900 can implement one of two types of simple aligners for the high confidence, low computation processing path: a simple aligner that skips exact matches or a simple aligner that skips single mis-matches. A simple aligner that skips single matches allows zero or one mismatch. The "Skip Exact Matches" data shows the reduced processing cycles when the conventional (blue) path is skipped if the 16 bases of the current iteration exactly match the 16 bases of the reference sequence at the previously determined reference position. The "Skip Single Mismatches" data shows the reduced processing cycles when the conventional (blue) path is skipped if the 16 bases of the current iteration align to the 16 bases of the reference sequence at the previously determined reference position with at most one mismatch. FIG. 9C shows that compared to the baseline, when the method 900 utilizes the simple aligner that skipped conventional processing when single mismatches were detected in the high confidence, low computation processing path, the runtime is reduced by three times. Note these numbers were generated by a prototype processor that does not include all processing steps, and as a result, is a projection of expectations.

FIG. 10 is another flowchart of an example method 1000 for performing a real-time secondary analysis. The method 1000 and the method 900 shown in FIG. 9A can implement the same low confidence, high computation processing path and different high confidence, low computation processing path. The high confidence, low computation processing path of the method 1000 generates the MapQ score after simple alignment and uses the MapQ score to determine whether to continue processing in the high confidence, low computation processing path or to return to the low confidence, high processing path.

A high percentage of the runtime occurs on a small percentage of the reads. In some embodiments, the low confidence, high computation processing path of the method 900 or 1000 can skip the align and store steps if the confidence of success as determined using a metric is low. In one embodiment, a metric may be generated which indicates the number of candidate positions at which a subsequence may align to the reference sequence. The confidence of alignment success will be low if the number of candidate positions is high. In a second embodiment, the confidence of alignment success will be low if the diversity of bases in the sequence is low. The diversity of bases may be determined, for example, by counting the number of unique n-mers in the subsequence, where the n-mer is a sequence of bases in the subsequence that has length less than or equal to the length of the subsequence itself.

Alternative Embodiment—Variant Caller

Figure 11A:
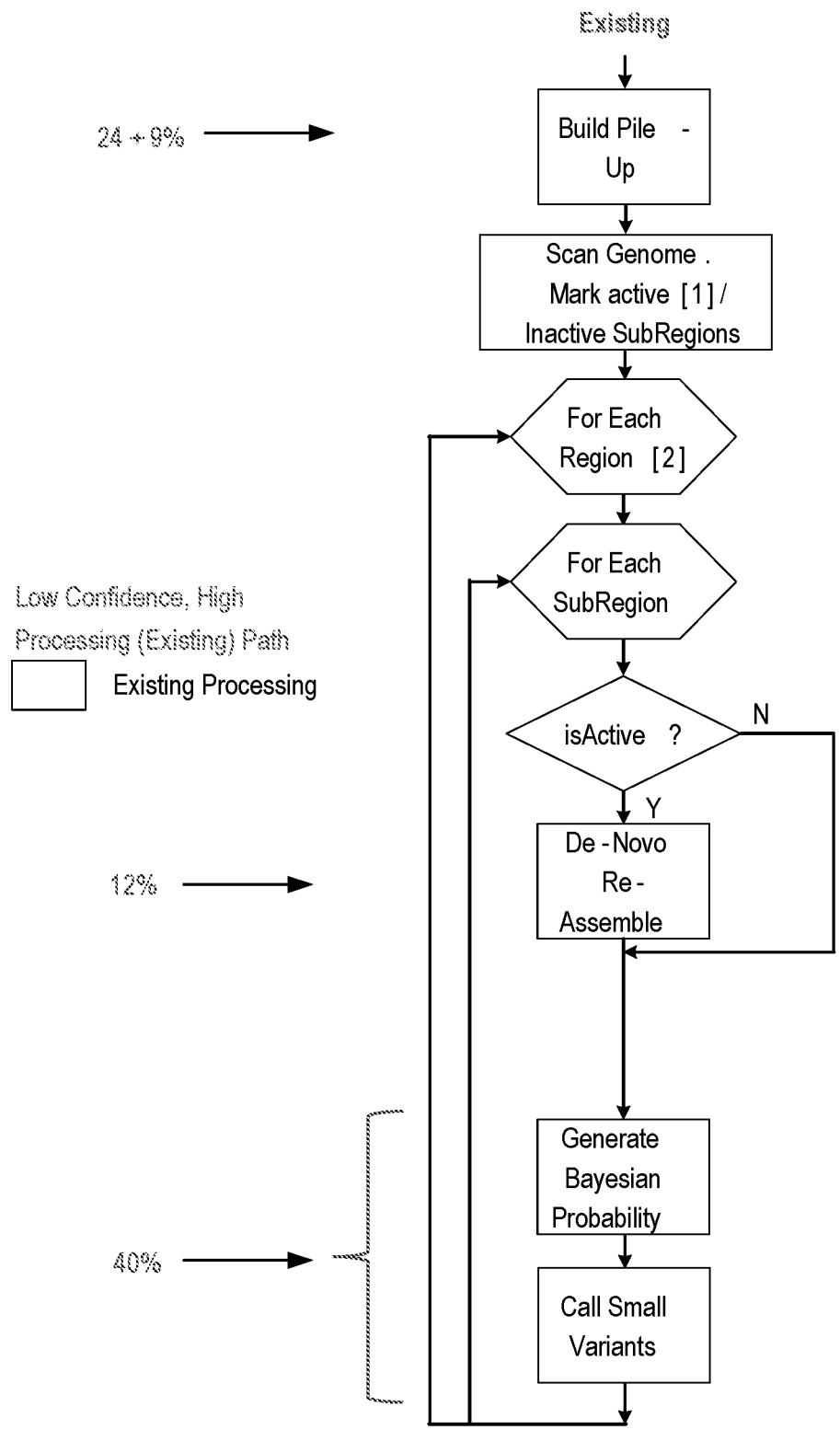
FIGS. 11A and 11B compare an existing variant caller (FIG. 11A) to a variant caller that uses high confidence, low processing path as described herein (FIG. 11B).
Figure 11B:
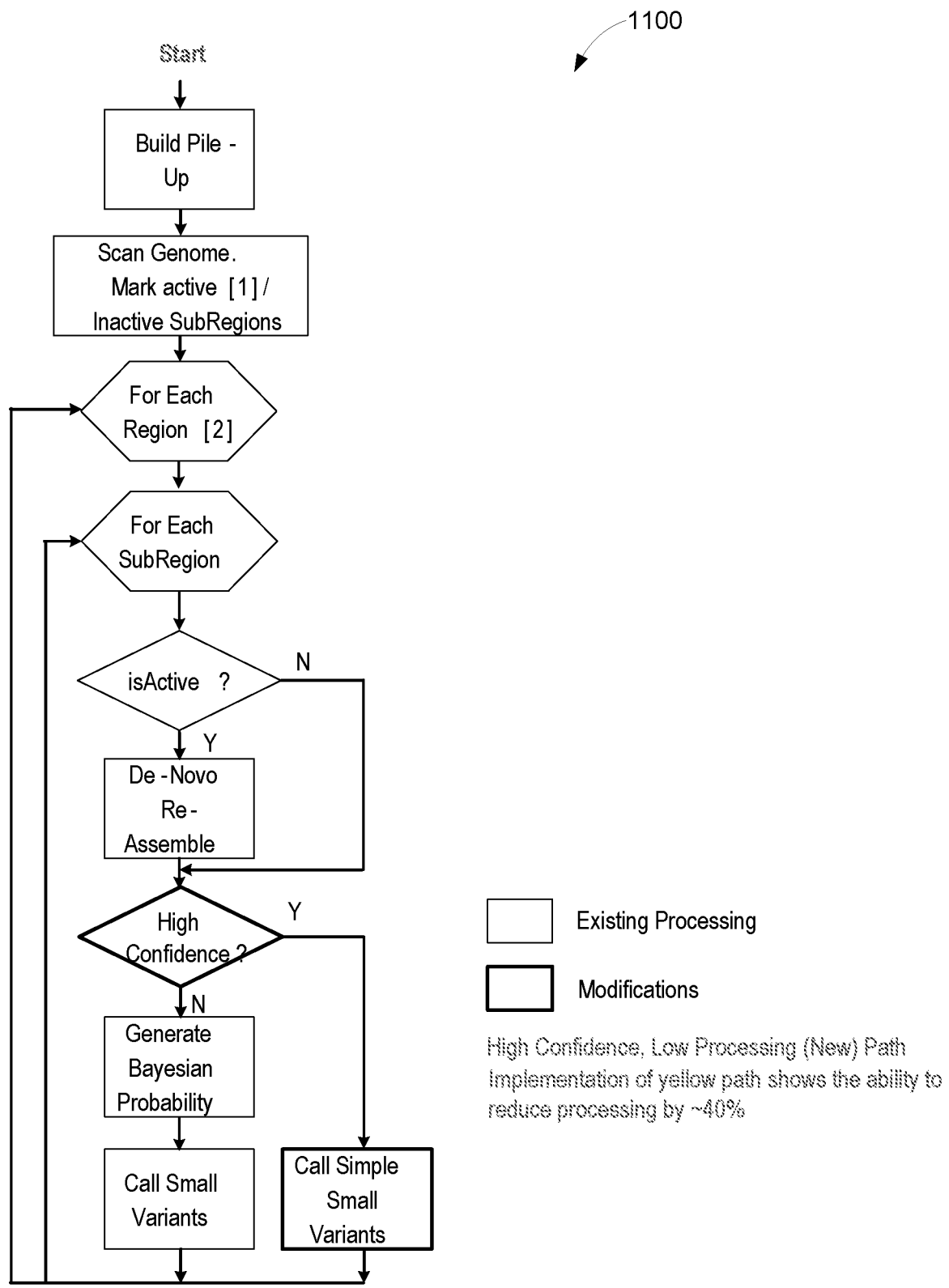

FIGS. 11A and 11B show a simplified flow diagram of an existing variant calling method, the Strelka small variant caller (FIG. 11A), and a variant calling method of the present disclosure (FIG. 11B). FIG. 11A shows that the small variant caller uses the pile-up information generated from the aligner as an input. From the pile-up, the small variant caller identifies regions of sequence variation known as active regions. Next, de novo re-assembly may be applied to the active regions. At each genomic position, probabilities are generated to determine the likelihood that a sequenced polynucleotide at a genomic position is an A, C, T, or G. From these probabilities, a variant may be detected.

FIG. 11B shows an embodiment of the variant caller as disclosed in the current invention. In this embodiment, a metric is generated to determine if a polynucleotide at a genomic position can be determined with high confidence. For example, a high confidence decision could be generated if all polynucleotides at a given genomic position are the same. Alternatively, a high confidence decision could be generated if the number of polynucleotides of the same type at a genomic position is higher than a threshold. Alternative metrics for determining high confidence can also be implemented. If the polynucleotide can be determined with high confidence, then the formulation of the probabilities may be skipped and a simple variant calling step may be executed. For example, a simple variant caller may call any variant that is detected with high confidence.

The generation of probabilities step and the variant calling step of an existing variant calling method can combined require up to 40% of the computing and processing of the variant caller. FIG. 11B shows a variant calling method 1100 that implements both the low confidence, high computation processing path of an existing variant calling method and a high confidence, low computation processing path. By adding the high confidence, low computation processing path, the Strelka variant caller was optimized and processing was reduced by nearly 40%. A high confidence, low computation processing path can be added to alternative variant callers.

As shown in FIG. 7B, a variant caller may be executed within the iterative processing window. The variant caller of FIG. 11A or FIG. 11B may be executed iteratively within the iterative processing window. Additionally, more than one type of variant caller may be executed within the iterative processing window. For example, a small variant caller, such as Strelka, and alternative variant callers, such as structural variant callers or copy number variant callers, may be executed within the iterative processing window.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for sequencing polynucleotides, comprising:
a sequencing apparatus configured to determine the nucleotide sequence of a polynucleotide; and
a processor configured to:
execute instructions that perform a method comprising:
receiving a first nucleotide subsequence of the polynucleotide from the sequencing apparatus;
comparing the first nucleotide subsequence to a reference sequence to determine whether the first nucleotide subsequence aligns to the reference sequence with a first confidence;
receiving a second nucleotide subsequence of the polynucleotide from the sequencing apparatus, wherein the second nucleotide subsequence comprises the first nucleotide subsequence plus one or more additional nucleotides;
comparing the one or more additional nucleotides in the second nucleotide subsequence to the reference sequence if the first nucleotide subsequence is aligned to the reference sequence at the first confidence; and
providing a metric to enable terminating receipt of nucleotide subsequences from the sequencing apparatus based in part on the comparison of the additional nucleotides to the reference sequence.

2. The system of claim 1, wherein the first confidence depends on a number of mismatches a probability of a correct match, a number of candidate positions at which the first nucleotide subsequence aligns to the reference sequence, or a diversity of bases in the first nucleotide subsequence.

3. The system of claim 1, wherein comparing the one or more additional nucleotides in the second nucleotide subsequence to the reference sequence comprises a simple alignment process, the simple alignment process being more computationally efficient, in memory usage or the number of computation operations, than a process used to align the first nucleotide subsequence with the reference sequence.

4. The system of claim 3, wherein the processor is further configured to determine a simple alignment score based on the simple alignment process.

5. The system of claim 3, wherein the simple alignment process aligns only the one or more additional nucleotides in the second nucleotide subsequence to the reference sequence based in part on a first plurality of candidate locations resulting from comparing the first nucleotide subsequence to the reference sequence.

6. The system of claim 1, wherein the processor is further configured to store data corresponding to at least one of a first plurality of candidate locations resulting from comparing the first nucleotide subsequence to the reference sequence.

7. The system of claim 6, wherein comparing the one or more additional nucleotides in the second nucleotide subsequence to the reference sequence comprises comparing the second nucleotide subsequence with corresponding sequences of the second nucleotide subsequence on the reference sequence based on the first plurality of candidate locations.

8. The system of claim 1, wherein the processor is further configured to store data corresponding to at least one of a second plurality of candidate locations resulting from comparing the second nucleotide subsequence to the reference sequence.

9. The system of claim 8, wherein the processor is further configured to determine a mapping quality (MapQ) score for each of the second plurality of candidate locations.

10. The system of claim 1, wherein determining whether the first nucleotide subsequence aligns to the reference sequence is initiated before the sequencing reactions are completed.

11. The system of claim 1, wherein the processor is further configured to perform variant calling for the first nucleotide subsequence or the second nucleotide subsequence.

12. The system of claim 11, wherein performing the variant calling comprises:
performing variant calling using a first variant calling process or a second variant calling process, wherein the second variant calling process is more time- or computing resource-efficient than the first variant calling process in variant calling of the second nucleotide subsequence.

13. The system of claim 11, wherein the variant calling is performed using the output of: a process used to align the first nucleotide subsequence with the reference sequence, or a process used to compare the one or more additional nucleotides in the second nucleotide subsequence to the reference sequence, based on a variant calling metric.

14. The system of claim 13, wherein the variant calling metric is determined based on a number of different base types called at a position of the reference sequence.

15. The system of claim 1, wherein processing the second nucleotide subsequence is initiated before the sequencing reactions are completed.

16. The system of claim 1, wherein the sequencing apparatus implements sequencing-by-synthesis.

17. The system of claim 1, further comprising aligning the entire second nucleotide subsequence to the reference sequence if the first nucleotide subsequence is not aligned to the reference sequence at the first confidence.

18. The system of claim 1, wherein the metric indicates whether variant calling has achieved a predetermined confidence.

19. The system of claim 1, wherein the metric indicates whether a particular target variant has been identified.

20. The system of claim 1, wherein the processor is further configured to terminate receipt of nucleotide subsequences from the sequencing apparatus based on the metric.

21. The method of claim 1, wherein the processor is further configured to terminate the sequencing run of the sequencing apparatus based on the metric.

22. A computer-implemented method for determining the sequence of a polynucleotide having nucleotide subsequences, the method comprising:
receiving a first nucleotide subsequence of a read from a sequencing apparatus during a sequencing run;
performing a secondary analysis of the first nucleotide subsequence of the read based on a reference sequence using a first process or a second process, wherein the second process is more time- or computing resource-efficient than the first process in performing the secondary analysis, and wherein the secondary analysis comprises:
comparing the first nucleotide subsequence to the reference sequence to determine a first subsequence of the reference sequence that has a high degree of similarity to the first nucleotide subsequence; and
providing a metric to enable terminating receipt of nucleotide subsequences from the sequencing apparatus based in part on a result of the secondary analysis.

23. The method of claim 22, wherein performing the secondary analysis comprises processing the first nucleotide subsequence to determine a first plurality of candidate locations of the read that align to the reference sequence using:
the first process if the read is not aligned to the reference sequence in a previous iteration,
the second process if otherwise,
wherein the second process is more time- or computing resource-efficient than the first process to determine the first plurality of candidate locations of the read.

24. The method of claim 23, wherein processing the first nucleotide subsequence using the second process comprises performing a simple alignment to determine a simple alignment score.

25. The method of claim 23, wherein results of the secondary analysis comprises output of the first process, output of the second process, or any combination thereof.

26. The method of claim 22, wherein performing the secondary analysis comprises performing variant calling of the first nucleotide subsequence, comprising:
performing variant calling on the output of the first process or the second process using a first variant calling process or a second variant calling process, wherein the second variant calling process is more time- or computing resource-efficient than the first variant calling process in variant calling of the first nucleotide subsequence.

27. The method of claim 26, wherein results of the secondary analysis comprises output of the first variant calling process, output of the second variant calling process, or any combination thereof.

28. The method of claim 22, further comprising providing a user with results of the secondary analysis during the sequencing run.

29. The method of claim 28, wherein the results of the secondary analysis are provided to the user at fixed intervals.

30. The method of claim 28, wherein the results of the secondary analysis are provided to the user at request of the user.

31. The method of claim 22, wherein performing the secondary analysis comprises performing the secondary analysis of the first nucleotide subsequence of the read based on results from a prior sequencing interval of the sequencing run.

32. The method of claim 22, wherein the first nucleotide subsequence comprises one or more additional nucleotides compared to a previous iteration, wherein the first process aligns the entire first nucleotide subsequence to the reference sequence, and wherein the second process aligns the one or more additional nucleotides to the reference sequence based in part on results from the previous iteration.

33. The method of claim 22, wherein the metric indicates whether variant calling has achieved a predetermined confidence.

34. The method of claim 22, wherein the metric indicates whether a particular target variant has been identified.

35. The method of claim 22, further comprising terminating receipt of nucleotide subsequences from the sequencing apparatus based on the metric.

36. The method of claim 22, further comprising terminating the sequencing run of the sequencing apparatus based on the metric.

* * * * *